United States Patent
Calderwood et al.

Patent Number: 6,001,839
Date of Patent: Dec. 14, 1999

[54] SUBSTITUTED 4-AMINO-7H-PYRROLO [2,3,-D]-PYRIMIDINES AS PTK INHIBITORS

[75] Inventors: David J. Calderwood; David N. Johnston; Paul Rafferty; Helen L. Twigger, all of Nottingham, United Kingdom; Rainer Munschauer, Shrewsbury; Lee Arnold, Westborough, both of Mass.

[73] Assignee: BASF Aktiengesellschaft, Rheinland-Pfalz, Germany

[21] Appl. No.: 09/042,702

[22] Filed: Mar. 17, 1998

Related U.S. Application Data

[60] Provisional application No. 60/040,836, Mar. 19, 1997.

[51] Int. Cl.$^6$ .................. C07D 487/04; A61K 31/505
[52] U.S. Cl. ............................................. 514/258; 544/280
[58] Field of Search ............................ 544/280; 514/258

[56] References Cited

U.S. PATENT DOCUMENTS

| | | | |
|---|---|---|---|
| 5,593,997 | 1/1997 | Dow et al. | 514/258 |
| 5,639,757 | 6/1997 | Dow et al. | 514/261 |
| 5,665,721 | 9/1997 | Bhagwat et al. | 514/253 |
| 5,834,469 | 11/1998 | Elliott et al. | 514/249 |

FOREIGN PATENT DOCUMENTS

| | | |
|---|---|---|
| WO 96/10028 | 4/1996 | WIPO . |
| WO 96/40686 | 12/1996 | WIPO . |
| WO 97/28161 | 8/1997 | WIPO . |
| WO 97/32879 | 9/1997 | WIPO . |
| WO 97/34895 | 9/1997 | WIPO . |

OTHER PUBLICATIONS

Hanke, J.H., et al. "Discovery of a Novel, Potent, and Src Family–selective Tyrosine Kinase Inhibitor; Study of Lck–and FynT–dependent T Cell Activation". *J Biol Chem.* 271(2):695–701, 1996.

Primary Examiner—Mukund J. Shah
Assistant Examiner—Deepak Rao
Attorney, Agent, or Firm—Hamilton, Brook, Smith & Reynolds, P.C.

[57] ABSTRACT

Compounds of formula I

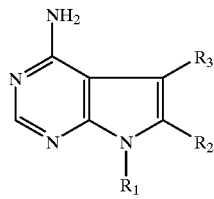

including pharmaceutically acceptable salts thereof in which
$R_1$ represents hydrogen, 2-phenyl-1,3-dioxan-5-yl, a $C_{1-6}$ alkyl group, a $C_{3-8}$ cycloalkyl group, a $C_{5-7}$ cycloalkenyl group or an (optionally substituted phenyl)$C_{1-6}$ alkyl group wherein the alkyl, cycloalkyl and cycloalkenyl groups are optionally substituted by one or more groups of formula $OR_A$ in which $R_A$ represents H or a $C_{1-6}$ alkyl group provided that a group of formula $OR_A$ is not located on the carbon attached to nitrogen;
$R_2$ represents hydrogen, a $C_{1-6}$ alkyl group, a $C_{3-8}$ cycloalkyl group, halo, hydroxy, an (optionally substituted phenyl) $C_{1-6}$ alkyl group, optionally substituted phenyl or $R_4$; and
$R_3$ represents a group of formula (a)

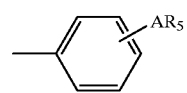

in which the phenyl ring is additionally optionally substituted and
A represents NH, O, NHSO$_2$, SO$_2$NH, a $C_{1-4}$ alkylene chain, NHCO, NHCO$_2$, CONH, NHCONH, CO$_2$ or S(O)$_p$ in which p is 0, 1 or 2, or A is absent and $R_5$ is attached directly to the phenyl ring;
and $R_5$ represents optionally substituted phenyl and, additionally, when A is absent $R_5$ represents a) a phthalimido group optionally substituted by halo or b) a pyrazolylamino group in which the pyrazole ring is optionally substituted by one or more of the following: hydroxy or optionally substituted phenyl;
$R_4$ represents a heterocyclic group; are described which are useful in treating proliferative diseases and disorders of the immune system in mammals. Processes to prepare these compounds and pharmaceutical compositions containing these compound are also described.

28 Claims, No Drawings

SUBSTITUTED 4-AMINO-7H-PYRROLO [2,3,-D]-PYRIMIDINES AS PTK INHIBITORS

RELATED APPLICATIONS

This application claims the benefit of U.S. Provisional Application Ser. No. 60/040,836, filed Mar. 19, 1997, the contents of which are incorporated herein by reference in their entirety.

This invention relates to novel substituted 4-amino-7H-pyrrolo[2,3-d]-pyrimidines having therapeutic activity as protein tyrosine kinase inhibitors, to pharmaceutical compositions containing these compounds and to processes for their preparation.

BACKGROUND OF THE INVENTION

Protein tyrosine kinases (PTKs) are enzymes which catalyse the phosphorylation of specific tyrosine residues in protein. The post-translational modification of these substrate proteins, often enzymes themselves, acts as a molecular switch regulating cell proliferation and activation. Abnormal PTK activity has been observed in many disease states including benign and malignant proliferative disorders as well as diseases resulting from inappropriate activation of the immune system (autoimmunity, allograft rejection and graft versus host disease). It is believed that compounds which selectively inhibit the responsible PTKs may be useful therapeutic agents.

Compounds of formula A

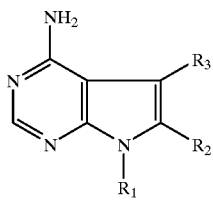

A in which $R_1$ is aryl, $R_2$ is hydrogen, lower alkyl or halo and $R_3$ is aryl are disclosed as inhibitors of the protein tyrosine kinase pp60$^{c\text{-}src}$ in WO96/10028. Compounds of formula A in which $R_1$ is unsubstituted or substituted cyclo-lower alkyl or cyclo-lower alkenyl and $R_2$ and $R_3$ are as previously defined are disclosed in co-pending application WO 97/28161. Compounds of formula A in which $R_1$ is lower alkyl or substituted lower alkyl and $R_2$ and $R_3$ are as previously defined are disclosed in co-pending application WO 97/32879.

Compounds of formula B

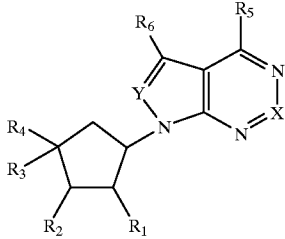

B wherein X is —N or $CR_7$, where $R_7$ is hydrogen, halogen, loweralkyl, loweralkoxy or -S-loweralkyl; Y is —N or —CH; $R_1$ and $R_2$ are each independently hydrogen, hydroxy, alkoxy, or acyloxy or $R_1$ and $R_2$ are both hydroxy protected with an individual hydroxy protecting group or with a single dihydroxy-protecting group or $R_1$ and $R_2$ are absent and there is a double bond between the carbon atoms to which $R_1$ and $R_2$ are attached; $R_3$ is hydrogen, hydroxy, loweralkyl or alkoxy; $R_4$ is inter alia (a) hydrogen, (b) amino, (c) halogen, (d) hydroxy or $R_3$ and $R_4$ taken together are =O, or taken together with the carbon atom to which they are attached, form a spirocyclic ring; $R_5$ is inter alia hydrogen, loweralkyl or amino; and $R_6$ is inter alia loweralkyl, aryl, heteroaryl or heteroarylalkyl; are disclosed as being adenosine kinase inhibitors in WO 96/40686.

SUMMARY OF THE INVENTION

The present invention provides compounds of formula I

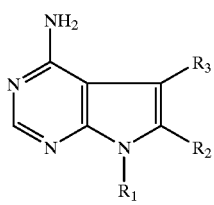

I including pharmaceutically acceptable salts thereof in which
$R_1$ represents hydrogen, 2-phenyl-1,3-dioxan-5-yl, a $C_{1-6}$ alkyl group, a $C_{3-8}$ cycloalkyl group, a $C_{5-7}$ cycloalkenyl group or an (optionally substituted phenyl)$C_{1-6}$ alkyl group wherein the alkyl, cycloalkyl and cycloalkenyl groups are optionally substituted by one or more groups of formula $OR_A$ in which $R_A$ represents H or a $C_{1-6}$ alkyl group provided that a group of formula $OR_A$ is not located on the carbon attached to nitrogen;

$R_2$ represents hydrogen, a $C_{1-6}$ alkyl group, a $C_{3-8}$ cycloalkyl group, halo, hydroxy, an (optionally substituted phenyl) $C_{1-6}$ alkyl group, optionally substituted phenyl or $R_4$; and $R_3$ represents a group of formula (a)

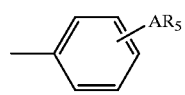

(a)

in which the phenyl ring is additionally optionally substituted and

A represents NH, O, NHSO$_2$, SO$_2$NH, a $C_{1-4}$ alkylene chain, NHCO, NHCO$_2$, CONH, NHCONH, CO$_2$ or S(O)$_p$ in which p is 0, 1 or 2, or A is absent and $R_5$ is attached directly to the phenyl ring;

and $R_5$ represents optionally substituted phenyl and, additionally, when A is absent $R_5$ represents a) a phthalimido group optionally substituted by halo or b) a pyrazolylamino group in which the pyrazole ring is optionally substituted by one or more of the following: hydroxy or optionally substituted phenyl;

$R_4$ represents a heterocyclic group selected from thienyl, benzo(b)thienyl, pyridyl, pyrazolyl, isoxazolyl, thiadiazolyl, oxadiazolyl, indazolyl, each of which is optionally substituted by one or more of the following: a $C_{1-6}$ alkyl group; a $C_{3-6}$ cycloalkyl group; a $C_{1-6}$ alkoxy group; a $C_{1-6}$ alkylthio group; hydroxy; optionally substituted phenyl; an (optionally substituted phenyl)$C_{1-6}$ alkyl group; an (optionally substituted phenyl)$C_{1-6}$ alkylthio group; or an (optionally substituted phenyl)$C_{1-6}$ alkoxy group;

wherein the term optionally substituted phenyl means phenyl optionally substituted by one or more of the following: a) a $C_{1-6}$ alkyl group, b) a $C_{1-6}$ alkoxy group, c) phenoxy, d) hydroxy, e) phenyl $C_{1-6}$ alkyl, f) halo, g) a group of formula $NR_{10} R_{11}$ in which $R_{10}$ and $R_{11}$ independently represent hydrogen, a $C_{1-6}$ alkyl group, phenyl, a $C_{1-6}$ alkanoyl group, a ($C_{1-6}$ alkoxy)carbonyl group, 5-hydroxy-1-phenyl-3-pyrazolyl or benzoyl which is optionally substituted by $C_{1-6}$ alkyl, $C_{1-6}$ alkoxy or halo h) a group of formula —$COR_9$ in which $R_9$ represents hydroxy, a $C_{1-6}$ alkoxy group, phenoxy or a group of formula $NR_{10}R_{11}$ in which $R_{10}$ and $R_{11}$ are as previously defined, i) a phthalimido group optionally substituted by halo, j) the phenyl ring is benz fused forming naphthyl or k) nitro.

In preferred compounds of formula I:

$R_1$ represents a $C_{1-6}$ alkyl group, a $C_{3-8}$ cycloalkyl group or an (optionally substituted phenyl)$C_{1-6}$ alkyl group wherein the alkyl and cycloalkyl groups are optionally substituted by one or more groups of formula $OR_A$ in which $R_A$ represents H or a $C_{1-6}$ alkyl group provided that a group of formula $OR_A$ is not located on the carbon attached to nitrogen;

$R_2$ represents hydrogen, a $C_{1-6}$ alkyl group, a $C_{3-8}$ cycloalkyl group, halo, hydroxy, an (optionally substituted phenyl) $C_{1-6}$ alkyl group, optionally substituted phenyl or $R_4$; and $R_3$ represents a group of formula (a)

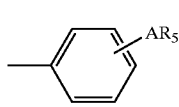

(a)

in which the phenyl ring is additionally optionally substituted and

A represents NH, O, $NHSO_2$, $SO_2NH$, a $C_{1-4}$ alkylene chain, NHCO, $NHCO_2$, CONH, NHCONH, $CO_2$ or $S(O)_p$ in which p is 0, 1 or 2, or A is absent and $R_5$ is attached directly to the phenyl ring;

and $R_5$ represents optionally substituted phenyl and, additionally, when A is absent $R_5$ represents a) a phthalimido group optionally substituted by halo or b) a pyrazolylamino group in which the pyrazole ring is optionally substituted by one or more of the following: hydroxy or optionally substituted phenyl;

$R_4$ represents a heterocyclic group selected from thienyl, benzo(b)thienyl, pyridyl, pyrazolyl, isoxazolyl, thiadiazolyl, oxadiazolyl, indazolyl, each of which is optionally substituted by one or more of the following: a $C_{1-6}$ alkyl group; a $C_{3-6}$ cycloalkyl group; a $C_{1-6}$ alkoxy group; a $C_{1-6}$ alkylthio group; hydroxy; optionally substituted phenyl; an (optionally substituted phenyl)$C_{1-6}$ alkyl group; an (optionally substituted phenyl)$C_{1-6}$ alkylthio group; or an (optionally substituted phenyl)$C_{1-6}$ alkoxy group;

wherein the term optionally substituted phenyl means phenyl optionally substituted by one or more of the following: a) a $C_{1-6}$ alkyl group, b) a $C_{1-6}$ alkoxy group, c) phenoxy, d) hydroxy, e) phenyl $C_{1-6}$ alkyl, f) halo, g) a group of formula $NR_{10} R_{11}$ in which $R_{10}$ and $R_{11}$ independently represent hydrogen, a $C_{1-6}$ alkyl group, phenyl, a $C_{1-6}$ alkanoyl group, a ($C_{1-6}$ alkoxy)carbonyl group, 5-hydroxy-1-phenyl-3-pyrazolyl or benzoyl which is optionally substituted by $C_{1-6}$ alkyl, $C_{1-6}$ alkoxy or halo h) a group of formula —$COR_9$ in which $R_9$ represents hydroxy, a $C_{1-6}$ alkoxy group, phenoxy or a group of formula $NR_{10}R_{11}$ in which $R_{10}$ and $R_{11}$ are as previously defined, i) a phthalimido group optionally substituted by halo, or j) the phenyl ring is benz fused forming naphthyl.

DETAILED DESCRIPTION OF THE INVENTION

Preferably $R_1$ represents a $C_{3-6}$ alkyl group (for example propyl, isopropyl, butyl, isobutyl, sec-butyl, tert-butyl, pentyl, isopentyl, neopentyl, tert-pentyl or hexyl), a $C_{3-8}$ cycloalkyl group (for example cyclopropyl, cyclobutyl, cyclopentyl cyclohexyl cycloheptyl or cyclooctyl), or a $C_{5-7}$ cycloalkenyl group (for example cyclopentenyl, cyclohexenyl or cycloheptenyl) wherein the alkyl, cycloalkyl and cycloalkenyl groups are optionally substituted by one or more hydroxy groups provided that a hydroxy group is not located on the carbon attached to nitrogen. More preferably $R_1$ represents isopropyl, tert-butyl, 2-hydroxyethyl, cyclopentyl, neopentyl, 2-hydroxycyclopentyl, 4-hydroxycyclopent-2-enyl, 3-hydroxycyclopentyl, 2,3,4-trihydroxycyclopentyl, 1,3-dihydroxyprop-2-yl, or 2,3-dihydroxypropyl.

Preferably $R_2$ represents hydrogen, or halo (for example chloro, bromo or iodo). More preferably $R_2$ represents hydrogen or chloro.

Preferably $R_3$ represents a group of formula (a)

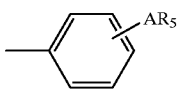

(a)

in which the phenyl ring is additionally optionally substituted and

A represents O, $NHSO_2$, NHCO, or $S(O)_p$ in which p is 0, 1 or 2, and $R_5$ represents optionally substituted phenyl. More preferably A represents O or S. Most preferably A represents O.

Most preferably $R_3$ represents 2-phenoxyphenyl, 3-phenoxyphenyl, 4-phenoxyphenyl, 4-(phenylthio)phenyl, 4-(4-methoxyphenoxy)phenyl, 4-(phenylsulphinyl)phenyl, 4-(phenylsulphonyl)phenyl,4-(4-hydroxyphenoxy)phenyl, 4-(benzenesulphonamido)phenyl, 4-(benzamido)phenyl, 4-(4-acetamidophenoxy)-phenyl), 4-(2-nitrophenoxy)phenyl,4-(4-aminophenoxy)phenyl, 4-(3-aminophenoxy)-phenyl, 4-(2-aminophenoxy)phenyl, 4-(3-acetamidophenoxy)phenyl, 4-[4-(N-methylacetamido)phenoxy]phenyl, 4-(2-acetamidophenoxy)phenyl, 4-(2-acetamido-4-nitrophenoxy)phenyl, 4-(3-carboxy-4-nitrophenoxy)phenyl, 4-(2-carboxy-4-nitrophenoxy)-phenyl, 4-(4-trifluoromethyl-2-nitrophenoxy)phenyl, 4-benzamido-3-methoxyphenyl, 4-benzamido-3-hydroxyphenyl, 4-benzenesulphonamido-3-methoxyphenyl, 4-benzenesulphonamido-3-hydroxyphenyl, 3-hydroxy-4-(4-tert-butylbenzenesulphonamido)phenyl, 4-(2-hydroxyphenoxy)phenyl, 4-(4-chlorobenzamido)-3-hydroxyphenyl, 4-(3-methoxy-4-nitrophenoxy)phenyl, 4-(4-methoxycarbonyl-2-nitrophenoxy)-phenyl, 4-(4-carboxy-2-nitrophenoxy)phenyl, 4-(5-chloro-2-nitrophenoxy)phenyl, or 4-[4-nitro-2-(2,2-dimethylpropionamido)phenoxy]phenyl.

In one preferred group of compounds of formula I
$R_1$ represents methyl, ethyl, propyl, isopropyl, butyl, tert-butyl, benzyl, or 2-hydroxyethyl;
$R_2$ represents hydrogen, methyl, halo, hydroxy or phenyl and $R_3$ represents, 2-phenoxyphenyl, 3-phenoxyphenyl, 4-phenoxyphenyl, 4-(4-chloro-N-phthalimido)-3-tolyl, 3-chloro-4-(3-chlorophenoxy)phenyl, 4-(4-methylaminophenyl amino)phenyl, 4-(4-methylaminophenylamino)-2-methoxyphenyl, 4-(4-methylaminobenzyl)phenyl, 4-anilino-2-methoxyphenyl, 3-hydroxy-4-(4-methylbenzamido)phenyl, 3-hydroxy-4-(2-methoxybenzamido)phenyl, 4-(4-chlorobenzamido)-3-hydroxyphenyl, 3-hydroxy-4-(2-naphthalenesulphonamido)phenyl, 3-hydroxy-4-[4-(tert-butyl)-benzenesulphonamido]phenyl, 4-[N-(5-hydroxy-1-phenylpyrazol-3-yl)amino]phenyl, or 4-phenoxycarbonylamino-3-hydroxyphenyl.

A second preferred group of compounds of formula I is represented by formula Ib

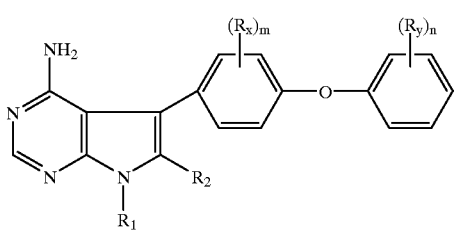

Ib and pharmaceutically acceptable salts thereof
in which $R_1$ represents hydrogen, a $C_{1-6}$ alkyl group, a $C_{3-8}$ cycloalkyl group, a $C_{5-7}$ cycloalkenyl group or an (optionally substituted phenyl)$C_{1-6}$ alkyl group wherein the alkyl, cycloalkyl and cycloalkenyl groups are optionally substituted by one or more groups of formula $OR_A$ in which $R_A$ represents H or a $C_{1-6}$ alkyl group provided that a group of formula $OR_A$ is not located on the carbon attached to nitrogen;

$R_2$ represents hydrogen or halo;

$R_x$ represents a $C_{1-6}$ alkyl group, a $C_{1-4}$ alkoxy group, halo, or hydroxy;

$R_y$ represents a $C_{1-6}$ alkyl group, a $C_{1-4}$ alkoxy group, halo, hydroxy, nitro, or a group of formula $NR_{10}R_{11}$ in which $R_{10}$ and $R_{11}$ independently represent hydrogen, a $C_{1-6}$ alkyl group, phenyl, a $C_{1-6}$ alkanoyl group, a ($C_{1-6}$ alkoxy)carbonyl group or $R_y$ represents a group of formula —$COR_9$ in which $R_9$ represents hydroxy, a $C_{1-6}$ alkoxy group, phenoxy or a group of formula $NR_{10}R_{11}$ in which $R_{10}$ and $R_{11}$ are as previously defined; and m and n independently represent 0, 1 or 2.

Preferred values of the substituents in compounds of formula Ib are given below.

Preferably $R_1$ represents a $C_{1-6}$ alkyl group, a $C_{3-8}$ cycloalkyl group, a $C_{5-7}$ cycloalkenyl group wherein the alkyl, cycloalkyl and cycloalkenyl groups are optionally substituted by one or more groups of formula $OR_A$ in which $R_A$ represents H or a $C_{1-6}$ alkyl group provided that a group of formula $OR_A$ is not located on the carbon attached to nitrogen. More preferably $R_1$ represents isopropyl, tert-butyl, 2-hydroxyethyl, cyclopentyl, neopentyl, 2-hydroxycyclopentyl, 4-hydroxycyclopent-2-enyl, 3-hydroxycyclopentyl, 2,3,4-trihydroxycyclopentyl, 1,3-dihydroxyprop-2-yl, or 2,3-dihydroxypropyl.

Preferably $R_2$ represents hydrogen or chloro.

Preferably $R_x$ represents hydroxy or a $C_{1-4}$ alkoxy group. More preferably $R_x$ represents hydroxy or methoxy.

Preferably $R_y$ represents a $C_{1-4}$ alkyl group, a $C_{1-4}$ alkoxy group, nitro, acetamido, amino, N-methylacetamido, carboxy, hydroxy or halo.

Preferably m represents 0 or 1. More preferably m represents 0.

Preferably n represents 0 or 1. More preferably n represents 0 or 1 and $R_y$ represents hydroxy, amino or acetamido.

It will be understood that any group mentioned herein which contains a chain of three or more atoms signifies a group in which the chain may be straight or branched. For example, an alkyl group may comprise propyl, which includes n-propyl and isopropyl, and butyl, which includes n-butyl, sec-butyl, isobutyl and tert-butyl. The term 'halo' as used herein signifies fluoro, chloro, bromo and iodo.

Compounds of formula I may exist as salts with pharmaceutically acceptable acids. The present invention includes such salts. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. These salts may be prepared by methods known to those skilled in the art.

Certain compounds of formula I which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formula I may exist in more than one physical form (for example different crystal forms) and the present invention includes each physical form (for example each crystal form) of compounds of formula I and mixtures thereof.

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

Certain compounds of formula I may contain one or more chiral centres, and exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of formula I and mixtures thereof.

Specific compounds of formula I are:

4-amino-5-(2-phenoxyphenyl)-7-(tert-butyl)pyrrolo[2,3-d]pyrimidine
4-amino-5-(3-phenoxyphenyl)-7-(tert-butyl)pyrrolo[2,3-d]pyrimidine
4-amino-7-methyl-5-(4-phenoxyphenyl)pyrrolo[2,3-d]pyrimidine
4-amino-5-(4-phenoxyphenyl)-6-phenyl-7-(tert-butyl)pyrrolo[2,3-d]pyrimidine
4-amino-6-methyl-5-(4-phenoxyphenyl)-7-(tert-butyl)pyrrolo[2,3-d]pyrimidine
4-amino-6-hydroxy-5-(4-phenoxyphenyl)-7-(tert-butyl)pyrrolo[2,3-d]pyrimidine
4-amino-7-butyl-5-(4-phenoxyphenyl)pyrrolo[2,3-d]pyrimidine
4-amino-5-[3-chloro-4-(3-chlorophenoxy)phenyl]-7-(tert-butyl)pyrrolo[2,3-d]pyrimidine
4-amino-5-[4-(4-methylaminophenylamino)phenyl]-7-(tert-butyl)pyrrolo[2,3-d]pyrimidine
4-amino-5-[4-(4-methylaminophenylamino)-2-methoxyphenyl]-7-(tert-butyl)pyrrolo[2,3-d]pyrimidine
4-amino-5-[4-(4-methylaminobenzyl)phenyl]-7-(tert-butyl)pyrrolo[2,3-d]pyrimidine
4-amino-5-[3-hydroxy-4-(4-methylbenzamido)phenyl]-7-(tert-butyl)pyrrolo[2,3-d]pyrimidine
4-amino-5-[3-hydroxy-4-(2-methoxybenzamido)phenyl]-7-(tert-butyl)pyrrolo[2,3-d]pyrimidine
4-amino-5-[4-(4-(4-chlorobenzamido)-3-hydroxyphenyl]-7-(tert-butyl)pyrrolo[2,3-d]pyrimidine
4-amino-5-[3-hydroxy-4-(2-naphthalenesulphonamido)phenyl]-7-(tert-butyl)pyrrolo[2,3-d]pyrimidine
4-amino-5-{3-hydroxy-4-[4-(tert-butyl)benzenesulphonamido]phenyl}-7-(tert-butyl)pyrrolo[2,3-d]pyrimidine
4-amino-5-{4-[N-(5-hydroxy-1-phenylpyrazol-3-yl)amino]phenyl}-7-(tert-butyl)pyrrolo[2,3-d]pyrimidine
4-amino-5-(4-phenoxycarbonylamino-3-hydroxyphenyl)-7-(tert-butyl)pyrrolo[2,3-d]pyrimidine
4-amino-5-[4-(4-chloro-N-phthalimido)-3-methylphenyl]-7-(tert-butyl)pyrrolo[2,3-d]pyrimidine
4-amino-5-[4-(2-methylphenoxy)phenyl]-7-(tert-butyl)pyrrolo[2,3-d]pyrimidine
4-amino-5-[4-(3-methylphenoxy)phenyl]-7-(tert-butyl)pyrrolo[2,3-d]pyrimidine
4-amino-5-[4-(2-methoxyphenoxy)phenyl]-7-(tert-butyl)pyrrolo[2,3-d]pyrimidine
4-amino-5-[4-(3-methoxyphenoxy)phenyl]-7-(tert-butyl)pyrrolo[2,3-d]pyrimidine
4-amino-5-[4-(2-chlorophenoxy)phenyl]-7-(tert-butyl)pyrrolo[2,3-d]pyrimidine
4-amino-5-[4-(3-chlorophenoxy)phenyl]-7-(tert-butyl)pyrrolo[2,3-d]pyrimidine
4-amino-5-[4-(2-ethoxycarbonylphenoxy)phenyl]-7-(tert-butyl)pyrrolo[2,3-d]pyrimidine
4-amino-5-[4-(3-ethoxycarbonylphenoxy)phenyl]-7-(tert-butyl)pyrrolo[2,3-d]pyrimidine
4-amino-5-[4-(2-carbamoylphenoxy)phenyl]-7-(tert-butyl)pyrrolo[2,3-d]pyrimidine
4-amino-5-[4-(3-carbamoylphenoxy)phenyl]-7-(tert-butyl)pyrrolo[2,3-d]pyrimidine
4-amino-5-[4-(2-hydroxyphenoxy)phenyl]-7-(tert-butyl)pyrrolo[2,3-d]pyrimidine
4-amino-5-[4-(3-hydroxyphenoxy)phenyl]-7-(tert-butyl)pyrrolo[2,3-d]pyrimidine
4-amino-5-(2-methyl-4-phenoxyphenyl)-7-(tert-butyl)pyrrolo[2,3-d]pyrimidine
4-amino-5-(3-methyl-4-phenoxyphenyl)-7-(tert-butyl)pyrrolo[2,3-d]pyrimidine
4-amino-5-(2-methoxy-4-phenoxyphenyl)-7-(tert-butyl)pyrrolo[2,3-d]pyrimidine
4-amino-5-(3-methoxy-4-phenoxyphenyl)-7-(tert-butyl)pyrrolo[2,3-d]pyrimidine
4-amino-5-(2-chloro-4-phenoxyphenyl)-7-(tert-butyl)pyrrolo[2,3-d]pyrimidine
4-amino-5-(3-chloro-4-phenoxyphenyl)-7-(tert-butyl)pyrrolo[2,3-d]pyrimidine
4-amino-5-(2-ethoxycarbonyl-4-phenoxyphenyl)-7-(tert-butyl)pyrrolo[2,3-d]pyrimidine
4-amino-5-(3-ethoxycarbonyl-4-phenoxyphenyl)-7-(tert-butyl)pyrrolo[2,3-d]pyrimidine
4-amino-5-(2-carbamoyl-4-phenoxyphenyl)-7-(tert-butyl)pyrrolo[2,3-d]pyrimidine
4-amino-5-(3-carbamoyl-4-phenoxyphenyl)-7-(tert-butyl)pyrrolo[2,3-d]pyrimidine
4-amino-5-(2-hydroxy-4-phenoxyphenyl)-7-(tert-butyl)pyrrolo[2,3-d]pyrimidine
4-amino-5-(3-hydroxy-4-phenoxyphenyl)-7-(tert-butyl)pyrrolo[2,3-d]pyrimidine
4-amino-5-[2-chloro-4-(3-chlorophenoxy)phenyl]-7-(tert-butyl)pyrrolo[2,3-d]pyrimidine
4-amino-5-[2-methyl-4-(3-chlorophenoxy)phenyl]-7-(tert-butyl)pyrrolo[2,3-d]pyrimidine
4-amino-5-[3-methyl-4-(3-chlorophenoxy)phenyl]-7-(tert-butyl)pyrrolo[2,3-d]pyrimidine
4-amino-5-[2-methoxy-4-(3-chlorophenoxy)phenyl]-7-(tert-butyl)pyrrolo[2,3-d]pyrimidine
4-amino-5-[3-methoxy-4-(3-chlorophenoxy)phenyl]-7-(tert-butyl)pyrrolo[2,3-d]pyrimidine
4-amino-5-[2-ethoxycarbonyl-4-(3-chlorophenoxy)phenyl]-7-(tert-butyl)pyrrolo[2,3-d]pyrimidine
4-amino-5-[3-ethoxycarbonyl-4-(3-chlorophenoxy)phenyl]-7-(tert-butyl)pyrrolo[2,3-d]pyrimidine
4-amino-5-[2-carbamoyl-4-(3-chlorophenoxy)phenyl]-7-(tert-butyl)pyrrolo[2,3-d]pyrimidine
4-amino-5-[3-carbamoyl-4-(3-chlorophenoxy)phenyl]-7-(tert-butyl)pyrrolo[2,3-d]pyrimidine
4-amino-5-[2-hydroxy-4-(3-chlorophenoxy)phenyl]-7-(tert-butyl)pyrrolo[2,3-d]pyrimidine
4-amino-5-[3-hydroxy-4-(3-chlorophenoxy)phenyl]-7-(tert-butyl)pyrrolo[2,3-d]pyrimidine
4-amino-5-[2-chloro-4-(2-chlorophenoxy)phenyl]-7-(tert-butyl)pyrrolo[2,3-d]pyrimidine
4-amino-5-[2-chloro-4-(4-chlorophenoxy)phenyl]-7-(tert-butyl)pyrrolo[2,3-d]pyrimidine
4-amino-5-[3-chloro-4-(3-methylphenoxy)phenyl]-7-(tert-butyl)pyrrolo[2,3-d]pyrimidine
4-amino-5-[4-(3-carbethoxyphenoxy)-3-chlorophenyl]-7-(tert-butyl)pyrrolo[2,3-d]pyrimidine
4-amino-5-[4-(3-carbamoylphenoxy)-3-chlorophenyl]-7-(tert-butyl)pyrrolo[2,3-d]pyrimidine
4-amino-5-[3-chloro-4-(3-hydroxyphenoxy)phenyl]-7-(tert-butyl)pyrrolo[2,3-d]pyrimidine
4-amino-5-[3-methyl-4-(3-methylphenoxy)phenyl]-7-(tert-butyl)pyrrolo[2,3-d]pyrimidine
4-amino-5-[3-methoxy-4-(3-methoxyphenoxy)phenyl]-7-(tert-butyl)pyrrolo[2,3-d]pyrimidine
4-amino-5-[3-hydroxy-4-(3-hydroxyphenoxy)phenyl]-7-(tert-butyl)pyrrolo[2,3-d]pyrimidine
4-amino-5-[3-methyl-4-(3-methoxyphenoxy)phenyl]-7-(tert-butyl)pyrrolo[2,3-d]pyrimidine
4-amino-5-[3-methoxy-4-(3-methylphenoxy)phenyl]-7-(tert-butyl)pyrrolo[2,3-d]pyrimidine
4-amino-5-[2-methoxy-4-(3-methylphenoxy)phenyl]-7-(tert-butyl)pyrrolo[2,3-d]pyrimidine 4-amino-5-[2-methyl-4-(3-methoxyphenoxy)phenyl]-7-(tert-butyl)pyrrolo[2,3-d]pyrimidine 7-tert-butyl-5-(4-phenoxyphenyl)-7H-pyrrolo[2,3-d]pyrimidin-4-ylamine 7-tert-butyl-6-chloro-5-(4-phenoxyphenyl)-7H-pyrrolo[2,3-d]pyrimidin-4-ylamine 7-isopropyl-5-(4-phenoxyphenyl)-7H-pyrrolo[2,3-d]pyrimidin-4-ylamine 7-cyclopentyl-5-(4-phenoxyphenyl)-7H-pyrrolo[2,3-d]pyrimidin-4-ylamine 5-(4-biphenylyl)-7-tert-butyl-7H-pyrrolo[2,3-d]pyrimidin-4-ylamine 7-neopentyl-5-(4-phenoxyphenyl)-7H-pyrrolo[2,3-d]pyrimidin-4-ylamine 7-tert-butyl-5-[4-(phenylthio)phenyl]-7H-pyrrolo[2,3-d]pyrimidin-4-ylamine 7-tert-butyl-5-[4-(4-methoxyphenoxy)phenyl]-7H-pyrrolo[2,3-d]pyrimidin-4-ylamine 7-tert-butyl-5-[4-(phenylsulphinyl)phenyl]-7H-pyrrolo[2,3-d]pyrimidin-4-ylamine 7-tert-butyl-5-[4-(phenylsulphonyl)phenyl]-7H-pyrrolo[2,3-d]pyrimidin-4-ylamine 4-[4-(4-amino-7-tert-butyl-7H-pyrrolo[2,3-d]pyrimidin-5-yl)phenoxy]phenol N-[4-(4-amino-7-isopropyl-7H-pyrrolo[2,3-d]pyrimidin-5-yl)phenyl]benzenesulphonamide N-[4-(4-amino-7-isopropyl-7H-pyrrolo[2,3-d]pyrimidin-5-yl)phenyl]benzamide N-{4-[4-(4-amino-7-tert-butyl-7H-pyrrolo[2,3-d]pyrimidin-5-yl)phenoxy]-phenyl}acetamide 7-isopropyl-5-[4-(2-nitrophenoxy) phenyl]-7H-pyrrolo[2,3-d]pyrimidin-4-ylamine 5-[4-(4-aminophenoxy)phenyl]-7-tert-butyl-7H-pyrrolo[2,3-d]pyrimidin-4-ylamine 5-[4-(3-aminophenoxy)phenyl]-7-tert-butyl-7H-pyrrolo[2,3-d]pyrimidin-4-ylamine 5-[4-(2-aminophenoxy)phenyl]-7-isopropyl-7H-pyrrolo[2,3-d]pyrimidin-4-ylamine N-{3-[4-(4-amino-7-tert-butyl-7H-pyrrolo[2,3-d]pyrimidin-5-yl)phenoxy]phenyl}acetamide N-{4-[4-(4-amino-7-tert-butyl-7H-pyrrolo[2,3-d]pyrimidin-5-yl)phenoxy]phenyl}-N-methylacetamide N-{2-[4-(4-amino-7-isopropyl-7H-pyrrolo[2,3-d]pyrimidin-5-yl)phenoxy]phenyl}acetamide N-{2-[4-(4-amino-7-isopropyl-7H-pyrrolo[2,3-d]pyrimidin-5-yl)phenoxy]-5-nitrophenyl}acetamide 5-[4-(4-amino-7-isopropyl-7H-pyrrolo[2,3-d]pyrimidin-5-yl)phenoxy]-2-nitrobenzoic acid 2-[4-(4-amino-7-isopropyl-7H-pyrrolo[2,3-d]pyrimidin-5-yl)phenoxy]-5-nitrobenzoic acid 2-[4-amino-5-(4-phenoxyphenyl)-7H-pyrrolo[2,3-d]pyrimidin-7-yl]ethanol 2-[4-amino-5-(4-phenoxyphenyl)-7H-pyrrolo[2,3-d]pyrimidin-7-yl]cyclopentanol 4-[4-amino-5-(4-phenoxyphenyl)-7H-pyrrolo[2,3-d]pyrimidin-7-yl]cyclopent-2-enol 6-chloro-7-cyclopentyl-5-(4-phenoxyphenyl)-7H-pyrrolo[2,3-d]pyrimidin-4-ylamine 5-(4-phenoxyphenyl)-7-(2-phenyl-1,3-dioxan-5-yl)-7H-pyrrolo[2,3-d]pyrimidin-4-ylamine 3-[4-amino-5-(4-phenoxyphenyl)-7-pyrrolo[2,3-d]pyrimidin-7-yl]cyclopentanol 4-[4-amino-5-(4-phenoxyphenyl)-7H-pyrrolo[2,3-d]pyrimidin-7-yl]cyclopentan-1,2,3-triol 7-cyclopentyl-5-(2-phenoxyphenyl)-7H-pyrrolo[2,3-d]pyrimidin-4-ylamine 7-cyclopentyl-5-(3-phenoxyphenyl)-7H-pyrrolo[2,3-d]pyrimidin-4-ylamine 2-[4-amino-5-(4-phenoxyphenyl)-7H-pyrrolo[2,3-d]pyrimidin-7-yl]propan-1,3-diol 3-[4-amino-5-(4-phenoxyphenyl)-7H-pyrrolo[2,3-d]pyrimidin-7-yl]propan-1,2-diol N-[4-(4-amino-7-cyclopentyl-7H-pyrrolo[2,3-d]pyrimidin-5-yl)-2-methoxyphenyl]benzamide N-[4-(4-amino-7-cyclopentyl-7H-pyrrolo[2,3-d]pyrimidin-5-yl)-2-hydroxyphenyl]benzamide N-[4-(4-amino-7-cyclopentyl-7H-pyrrolo[2,3-d]pyrimidin-5-yl)-2-methoxyphenyl]benzenesulphonamide N-[4-(4-amino-7-cyclopentyl-7H-pyrrolo[2,3-d]pyrimidin-5-yl)-2-hydroxyphenyl]benzenesulphonamide N-[4-(4-amino-7-cyclopentyl-7H-pyrrolo[2,3-d]pyrimidin-5-yl)-2-hydroxyphenyl]-4-tert-butylbenzenesulphonamide 7-cyclopentyl-5-[4-(2-methoxy)phenoxyphenyl]pyrrolo[2,3-d]pyrimidin-4-ylamine 2-[4-(4-amino-7-cyclopentyl-7H-pyrrolo[2,3-d]pyrimidin-5-yl)phenoxy]phenol 7-isopropyl-5-[4-(3-methoxy-4-nitrophenoxy)phenyl]-7H-pyrrolo[2,3-d]pyrimidin-4-ylamine methyl 4-[4-(4-amino-7-isopropyl-7H-pyrrolo[2,3-d]pyrimidin-5-yl)phenoxy]-3-nitrobenzoate 4-[4-(4-amino-7H-pyrrolo[2,3-d]-pyrimidin-5-yl)phenoxy]phenol N-[4-(4-amino-7-cyclopentyl-7H-pyrrolo[2,3-d]pyrimidin-5-yl)-2-methoxphenyl]-4-tert-butylbenzenesulphonamide 7-cyclopentyl-5-[4-(2-methoxy)phenoxyphenyl]-7H-pyrrolo[2,3-d]pyrimidin-4-ylamine N-[4-(4-amino-7-cyclopentyl-7H-pyrrolo[2,3-d]pyrimidin-5-yl)-2-hydroxy-phenyl]-4-chlorobenzamide 5-(4-phenoxyphenyl)-7H-pyrrolo[2,3-d]pyrimidin-4-ylamine 5-[4-(5-chloro-2-nitrophenoxy)phenyl]-7-isopropyl-7H-pyrrolo[2,3-d]pyrimidin-4-ylamine and N-{2-[4-(4-amino-7H-pyrrolo[2,3-d]pyrimidin-5-yl)phenoxy]-5-nitrophenyl}-2,2-dimethylpropionamide and pharmaceutically acceptable salts thereof in the form, where appropriate of individual enantiomers, racemates, or other mixtures of enantiomers.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

The present invention also includes pharmaceutical compositions containing a therapeutically effective amount of a compound of formula I or a salt thereof together with a pharmaceutically acceptable diluent or carrier.

As used hereinafter, the term "active compound" denotes a compound of formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example, suppositories with cocoa butter or polyethylene glycol bases.

Pharmaceutical compositions may also be administered parenterally (for example subcutaneously, intramuscularly, intradermally and/or intravenously [such as by injection and/or infusion]) in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents [such as ethylene oxide]). Optionally one or more of the following pharmaceutically acceptable adjuvants suitable for parenteral administration may be added to parenteral dosage forms: local anaesthetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered close systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises the use of a compound of formula I as a medicament.

Both the Src and Syk families of kinases play pivotal roles in the regulation of immune function. The Src family currently includes Fyn, Lck, Fgr, Fes, Lyn, Src, Yes, Hck, and Blk. The Syk family is currently understood to include only Zap and Syk. The Janus family of kinases is involved in the transduction of growth factor and pro-inflammatory cytokine signals through a number of receptors. By virtue of their ability to inhibit one or more of these kinases, compounds of formula I may function as immunomodulatory agents useful for the maintenance of allografts and the treatment of autoimmune disorders. Through their ability to regulate T cell activation or the potentiation of an inflammatory process, these compounds could be used to treat such autoimmune diseases. Transplants due to rejection phenomena, either host versus graft for solid organs or graft versus host for bonemarrow, are limited by the toxicity of currently available immunosuprressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, Paget's disease, tumour-induced hyper-calcaemia and in the treatment of bone metastases.

A number of tyrosine kinases have been demonstrated to be protooncogenes. Chromosome breakage (at the Itk kinase break point on chromosome 5), translocation as in the case of the Abl gene with BCR (Philadelphia chromosome) or the truncation of others such as cKit, result in the creation of dysregulated proteins converting them from proto- to onco-gene products. In other tumors, oncogenesis is driven by an autocrine or exocrine ligand/growth factor receptor interaction. By inhibiting the tyrosine kinase activity of these proteins the disease process may be disrupted. Vascular restenosis is process of PDGF—dependent endothelial cell proliferation. Prophylactic inhibition of PDGFr kinase activity may be an efficacious strategy for preventing this phenomenon. Thus compounds of formula I which inhibit the kinase activity of c-kit, c-fms, EGFr, BCR, Abl, PDGFr, KDR/Flk-1, Fit-1, tie-1, tie-2 and other receptors may be of value in the treatment of benign and neoplastic proliferative diseases.

The compounds of formula I or a salt thereof or pharmaceutical compositions containing a therapeutically effective amount thereof may be used in the treatment of benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, myasthenia gravis and systemic lupus erythematosus; psoriasis, organ transplant rejection eg. kidney rejection, graft versus host disease, benign and neoplastic proliferative diseases human cancers such as lung, breast, stomach, bladder, colon, pancreas, ovarian, prostate and rectal cancer and leukaemia, and diseases involving inappropriate vascularization for example diabetic retinopathy, choroidal neovascularization due to age-related macular degeneration, and infantile hemangiomas in human beings. In addition, such inhibitors may be useful in the treatment of disorders involving VEGF mediated edema, ascites, and exudates, including for example mascular edema and adult respiratory distress syndrome (ADRS).

The compounds of the present invention may also be useful in the prophylaxis of the above diseases.

A further aspect of the present invention provides the use of a compound of formula I or a salt thereof in the manufacture of a medicament for treating proliferative diseases and/or disorders of the immune system in mammals, particularly human beings.

The present invention also provides a method of treating proliferative diseases and/or disorders of the immune system which comprises the administration of a therapeutically effective amount of a compound of formula I to a mammal, particularly a human being, in need thereof.

Processes for the preparation of compounds of formula I will now be described. These processes form a further aspect of the present invention. The processes are preferably carried out at atmospheric pressure.

Compounds of formula I may be prepared by condensing a compound of formula II

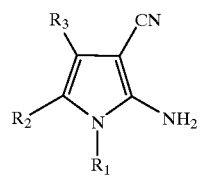

II in which $R_1$, $R_2$ and $R_3$ are as previously defined with formamide at a temperature in the range of 50 to 250° C. optionally in the presence of a catalyst for example 4-dimethylaminopyridine.

Compounds of formula I may be prepared by reacting a compound of formula I in which $R_1$ and $R_2$ are as previously defined and $R_3$ represents bromo or iodo with a compound of formula Ill

$$R_3B(OH)_2 \qquad\qquad III$$

in which $R_3$ is as initially defined, in the presence of a catalyst for example palladium (0) compounds eg. $Pd(PPh_3)_4$.

Compounds of formula I in which $R_1$ represents an alkyl group or an (optionally substituted phenyl) $C_{1-6}$ alkyl group may be prepared by alkylating a compound of formula IV

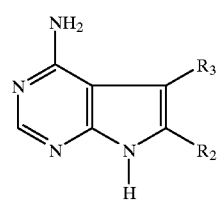

IV in which $R_2$ and $R_3$ are as previously defined with a compound of formula $R_1X$ in which $R_1$ represents an alkyl group or an (optionally substituted phenyl) $C_{1-6}$ alkyl group and X represents a leaving group for example halo or tosyloxy.

Compounds of formula I may be prepared by reacting a compound of formula V

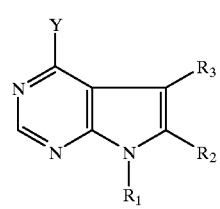

V in which $R_1$, $R_2$ and $R_3$ are as previously defined and Y represents a leaving group, for example halo or phenoxy, with ammonia or an ammonium salt, for example ammonium acetate, at a temperature in the range of 15–250° C., preferably in a pressure vessel.

Compounds of formula I in which $R_2$ represents chloro, bromo or iodo may be prepared by reacting a compound of formula VI

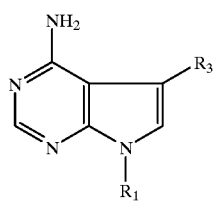

VI in which $R_1$ and $R_3$ are as previously defined with a halogenating agent for example an iodinating agent, e.g. N-iodosuccinimide or an brominating agent e.g. N-bromosuccinimide or a chlorinating agent e.g. N-chlorosuccinimide.

Compounds of formula I in which $R_3$ represents $AR_5$ in which A represents NHCO may be prepared by reacting a compound of formula VII

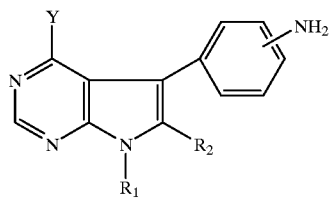

VII in which $R_1$ and $R_2$ are as previously defined and Y represents amino, with a compound of formula $R_5COX$ in which X represents a leaving group, for example chloro. Alternatively compounds of formula VII in which Y represents halo, for example chloro, may be reacted with a compound of formula $R_5COX$ and the product reacted with ammonia to give a compound of formula I. Analogous methods may be used when A represents $NHSO_2$.

Compounds of formula I in which $R_3$ represents $AR_5$ in which A represents O may be prepared by reacting a compound of formula VII

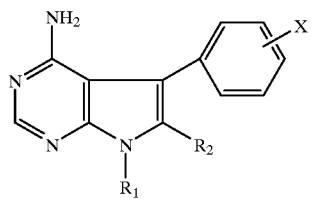

VIII in which $R_1$ and $R_2$ are as previously defined and X is halo with a compound of formula $R_5OH$ Compounds of formula I in which $R_3$ represents $AR_5$ in which A represents O may be prepared by reacting a compound of formula IX

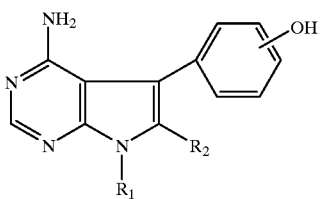

IX in which $R_1$ and $R_2$ are as previously defined with a compound of formula $R_5X$ in which X represents halo, preferably a halo activated by the presence of another substituent e.g. nitro.

Compounds of formula II may be prepared as shown in Scheme 1 in which IPA represents propan-2-ol, Scheme 1

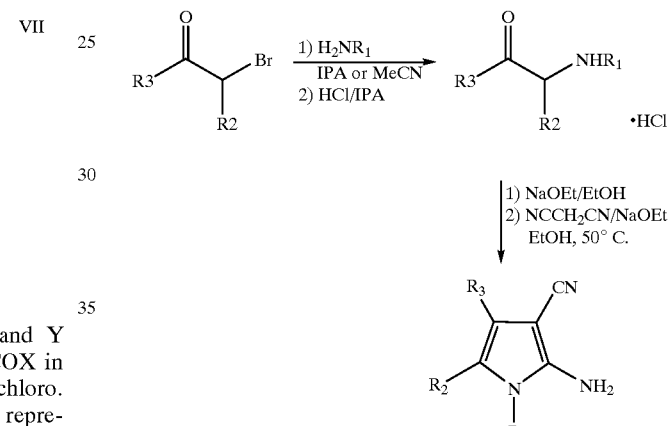

It will be appreciated by those skilled in the art that compounds of formula I may be converted into other compounds of formula I by known chemical reactions. For example, an alkoxy group may be cleaved to give hydroxy, nitro groups may be reduced to amines, amines may be acylated or sulphonylated and N-acyl compounds may be hydrolysed to amines. Compounds of formula I in which $R_3$ represents $AR_5$ in which A represents S may be oxidised to give compounds of formula I in which A represents SO and $SO_2$, respectively, by methods known to those skilled in the art.

Compounds of formula III are commercially available or may be prepared by methods known to those skilled in the art.

Compounds of formula IV in which $R_2$ represents hydrogen may be prepared as shown in Scheme 2. The amino group may be protected prior to the final step and then deprotected after the final step of scheme 2 by methods known to those skilled in the art. Compounds of formula IV in which $R_2$ is other than hydrogen may be prepared by analogous methods.

Scheme 2

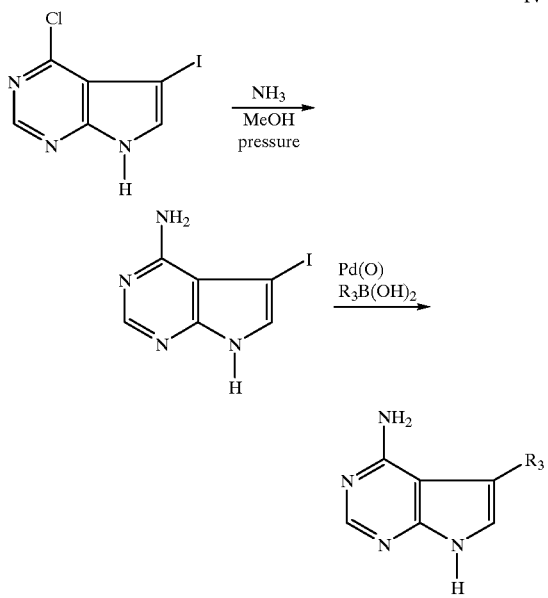

J. Med. Chem 1990, 33 1984

Alternatively in Scheme 2, $R_3$ may be coupled first, prior to amination. Alternatively a substituent $R_1$ as defined previously may be present prior to carrying out either process.

Compounds of formula V may be prepared as shown in Scheme 3

Scheme 3

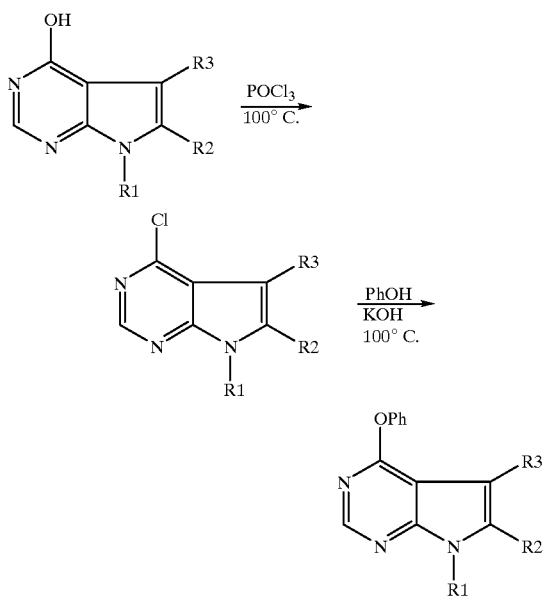

Compounds of formula VI in which $R_3$ represents hydrogen may be prepared as shown in Scheme 4. The starting material may be prepared as described in J.Med.Chem., 1988, 31, 390 and references cited therein. Compounds in which $R_3$ is other than hydrogen may be prepared by analogous methods.

Scheme 4

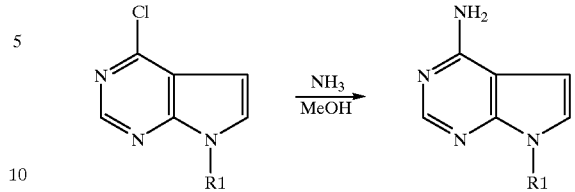

Compounds of formula VII may be prepared by coupling a 5-iodo compound in an analogous manner to that described for the preparation of compounds of formula IV.

It will be appreciated by those skilled in the art that in cases where a substituent is identical with, or similar to, a functional group which has been modified in one of the above processes that these substituents will require protection before the process is undertaken, followed by deprotection after the process. Otherwise competing side-reactions will occur. Alternatively, another of the processes described above, in which the substituent does not interfere, may be used. Examples of suitable protecting groups and methods for their addition and removal may be found in the textbook "Protective Groups in Organic Synthesis" by T. W. Green, John Wiley and Sons, 1981. For example suitable protecting groups for amines are formyl or acetyl.

The in vitro potency of compounds in inhibiting these tyrosine kinases may be determined by the procedures detailed below.

The potency of compounds can be determined by the amount of inhibition of the phosphorylation of an exogenous substrate (e.g., synthetic peptide (Z. Songyang et al., Nature. 373:536–539) on tyrosine by either lck or zap70 kinases by a test compound relative to control.

Expression of ZAP70

The baculoviral expression vector used was pVL1393. (Pharmingen, Los Angeles, Calif.) The nucleotide sequence encoding amino acids M(H)6 LVPRGS was placed 5' to the region encoding the entirety of ZAP70 (amino acids 1-619). The histidine residues enabled affinity purification of the protein (vide infra). The LVPRGS bridge constitutes a recognition sequence for proteolytic cleavage by thrombin, enabling removal of the affinity tag from the enzyme. SF-9 insect cells were infected at a multiplicity of infection of 0.5 and harvested 24 hours post infection.

Extraction and purification of ZAP70

SF-9 cells were lysed in a buffer consisting of 20 mM Tris, pH 8.0, 137 mM NaCl, 10% glycerol, 1% Triton X-100, 1 mM PMSF, 1 $\mu$g/ml leupeptin, 10 ug/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Lck source

Lck or truncated forms of Lck may be commercially obtained (e.g.from Upstate Biotechnology Inc. (Saranac Lake, N.Y.) and Santa Cruz Biotechnology Inc. (Santa Cruz, Calif.)) or purified from known natural or recombinant sources using conventional methods.

Assay

The protocol used for the measurement of tyrosine kinase activity has been previously described (Current Protocols in Immunol., John Wiley and Sons, pages 11.4.1–11.5.6. 1995). Briefly, all reactions were performed in a kinase buffer consisting of 50 mM MOPSO pH6.5, 2 mM MnCl$_2$, 5 mM DTT, 0.1% BSA, 2–211 μM ATP, 30–200 μM peptide, 5% DMSO and 33P ATP (8 Ci/mM). Compound and enzyme were mixed in the reaction vessel and the reaction initiated by addition of the ATP and substrate mixture. Following termination of the reaction by the addition of 2× stop buffer (20 mM) EDTA, a portion of the mixture was spotted on phosphocellulose filters. The spotted samples were washed 3 times in 75 mM phosphoric acid at room temperature for 5 to 15 minutes. Incorporation of radiolabel was assessed by liquid scintillation counting.

The compounds exemplified in the present invention have an IC$_{50}$ of less than 5 μm against Lck. Preferred compounds of the present invention are selective inhibitors of Lck.

Compounds of formula I may have therapeutic utility in the treatment of diseases involving both identified, including those not mentioned herein, and as yet unidentified PTKs which are inhibited by compounds of formula 1.

In Vitro Models for T-cell Activation:

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacture. Stimulator cells are mitotically inactivated by treatment with mitomycin c (Sigma) or gamma irradiation. Responder and stimulator cells are co-cultured at a ratio of two to one in the presence or absence of the test compound. Typically 10$^5$ responders are mixed with 5×10$^4$ stimulators and plated (200 μl volume) in a U bottom microtiter plate (Costar Scientific). The cells are cultured in RPMI 1640 supplemented with either heat inactivated fetal bovine serum (Hyclone Laboratories) or pooled human AB serum from male donors, 5×10$^{-5}$ M 2-mercaptoethanol and 0.5% DMSO. The cultures are pulsed with 0.5 μCi of $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model BALB/c mice are given 10 μg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α (TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 μg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at 6×10$^6$ per ml in tissue culture medium (RPMI 1640 supplemented with heat inactivated fetal bovine serum (Hyclone Laboratories) 5×10$^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model:J. Immunol 146 (4):1163–8, 1991). Briefly, mice or rats are immunized with an emulsion of myelin basic protein (MBP), or neurogenic peptide derivatives thereof, and CFA. Acute disease can be induced with the addition of bacterial toxins such asbordetella pertussis. Relapsing/remitting disease is induced by adoptive transfer of T-cells from MBP/peptide immunized animals.

CIA may be induced in DBA/1 mice by immunization with type II collagen (J. Immunol:142(7):2237–2243). Mice will develop signs of arthritis as early as ten days following antigen challenge and may be scored for as long as ninety days after immunization. In both the EAE and CIA models a compound may be administered either prophylactically or at the time of disease onset. Efficacious drugs should reduce severity and/or incidence.

Compounds can also be tested in mouse allograft models, either skin (reviewed Ann.Rev.Immunol., 10:333–58, 1992; Transplantation:57(12):1701–1706, 1994) or heart (Am.J.Anat.:113:273, 1963). Briefly, full thickness skin grafts are transplanted from C57BL/6 mice to BALB/c mice. The grafts are examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

The invention is illustrated by the following Examples which are given by way of example only. The final product of each of these Examples was characterised by one or more of the following procedures: high performance liquid chromatography; elemental analysis, nuclear magnetic resonance spectroscopy, infrared spectroscopy and high resolution mass spectroscopy.

EXAMPLE 1 a) Tert-butylamine (15 ml) was added with stirring to a solution of 2-bromo-4'-phenoxyacetophenone (12.7 g, prepared by bromination of 4'-phenoxyacetophenone according to Tetrahedron Letters, 1993, 34, 3177) in propan-2-ol and the mixture heated at 80° C. for 3 hours. The mixture was cooled to 0° C. and concentrated hydrochloric acid (10 ml) added. The suspension was stirred at ambient temperature for 18 hours and the solid collected by filtration to give 4'-phenoxy-2-(tert-butylamino)acetophenone hydrochloride (3.75 g), m.p. 210–212° C.

b) (1) 4'-Phenoxy-2-(tert-butylamino)acetophenone hydrochloride (3.75 g) was added in one portion to sodium ethoxide (prepared by dissolving sodium (93 mg) in ethanol (50 ml)) and the mixture was stirred at 40° C. for 30 minutes under nitrogen.

(2) In a separate flask sodium (331 mg) was dissolved in ethanol (50 ml) and malononitrile (858 mg) was added. The solution was stirred at ambient temperature for 5 minutes and then to this solution was added the solution of 4'-phenoxy-2-(tert-butylamino)acetophenone obtained in part (1) in one portion excluding the precipitated sodium chloride. The resultant mixture was heated at 50° C. for 3 hours and then at 800C for 2 hours. The solvent was removed under reduced pressure and the resultant oil was partitioned between water and ethyl acetate. The organic phase was separated, dried and evaporated to give a black solid. This solid was dissolved in hot ethanol and triturated with water, filtered and dried to give 2-amino-3-cyano-4-(4-phenoxyphenyl)-1-(tert-butyl)pyrrole.

c) A mixture of 2-amino-3-cyano-4-(4-phenoxyphenyl)-1-(tert-butyl)pyrrole (1.9 g), formamide (30 ml) and 4-dimethylaminopyridine (10 mg) was heated at 180° C. for 6 hours. The mixture was cooled to ambient temperature and water was added to precipitate a dark solid. The solid was collected by filtration, washed with water, then boiled up in ethanol and the insoluble material collected by hot filtration and dried. The solid was purified by preparative HPLC on a silica column using dichloromethane/propan-2-ol/ethanol, 98:1:1 as the mobile phase to give 7-tert-butyl-5-(4-phenoxyphenyl)-7H-pyrrolo[2,3-d]pyrimidin-4-ylamine (4-amino-5-(4-phenoxyphenyl)-7-(tert-butyl)pyrrolo[2,3-d]pyrimidine), m.p. 157–158° C. $^1$H NMR (d$^6$ DMSO) δ 8.15 (1H,s), 7.50–7.35 (4H,m), 7.30 (1H,s), 7.15 (1H,t), 7.10 (4H,m), 6.05 (2H,brs), 1.75 (9H,s).

EXAMPLE 2 a) A solution of 2-bromo-4'-phenoxyacetophenone (20.0 g) in toluene (150 ml) was added to a solution of isopropylamine (8.1 g) in toluene (100 ml) with stirring whilst keeping the temperature of the reaction mixture below 15° C. The mixture was stirred for 30 minutes at this temperature then stirred at ambient temperature for 20 minutes. The mixture was filtered and the residue was washed with ether. Oxalic acid (10.0 g) in ether (200 ml) was added to the combined filtrate and washings and the mixture filtered to give 2-isopropylamino-4'-phenoxyacetophenone oxalate. The oxalate salt was converted into the hydrochloride salt by treatment with concentrated hydrochloric acid. The solid salt was collected by filtration and used directly in the next stage.

b) The crude product (3.07 g) from a) above was suspended in methanol (60 ml) and malononitrile (1.0 g) was added with stirring. Nitrogen was bubbled through the suspension which was cooled in an ice-water bath and then potassium hydroxide (1.75 g) in water (2 ml) was added. After stirring for 15 minutes at this temperature, the mixture was heated to boiling under reflux and then boiled for one hour whilst nitrogen was bubbled through the mixture. The mixture was cooled and added to water (200 ml) through which nitrogen was bubbled. The gum obtained was dissolved in ether and separated off. The aqueous layer was extracted twice with ether and the combined ether layers were dried, filtered and evaporated to give a gum which solidified on standing under nitrogen overnight to give 2-amino-3-cyano-1-isopropyl-4-(4-phenoxy-phenyl)pyrrole.

c) The product (2.75 g) from b) was dissolved in formamide (120 ml) and ammonia was bubbled through whilst the mixture was stirred and heated in an oil bath at 200–205° C. for 2.5 hours. The mixture was cooled and added to ice-water then filtered to give a beige solid which was washed with water. This solid was found to be a mixture of the desired product and 4-amino-5-[4-(4-bromophenoxy)phenyl]-7-isopropylpyrrolo[2,3-d]pyrimidine. The mixture was hydrogenated in propan-1-ol, ammonium formate and 10% palladium on charcoal with stirring under nitrogen in a similar manner to that described in Example 5 to give a solid. This solid was purified by flash column chromatography on silica using ethyl acetate/triethylamine (19:1) as the mobile phase to give 7-isopropyl-5-(4-phenoxyphenyl)-7H-pyrrolo[2,3-d]-pyrimidin-4-ylamine, m.p. 155–156° C.

EXAMPLE 3 a) 4-Phenoxyacetophenone (150.0 g) was dissolved in acetic acid (2 l) and stirred at 50° C. whilst pyridinium tribromide (251.6 g) was added in portions. The brown solution was added to water (3 l) and the mixture extracted with toluene (1×800 ml and then 2×400 ml). The combined toluene extracts were washed with water and then with aqueous sodium bicarbonate solution until the effervescence ceased. The combined toluene extracts were separated, dried and filtered and used directly in part b) below.

b) The solution of 2-bromo-4'-phenoxyacetophenone in toluene obtained in a) was added to a solution of cyclopentylamine (154 ml) in toluene (1 l) with stirring under nitrogen over 1.5 hours whilst keeping the temperature below 5° C. The mixture was then stirred for 2.5 hours keeping the temperature below 10° C. and then the mixture was filtered. The filtrate was treated dropwise with concentrated hydrochloric acid (120 ml) whilst keeping the temperature below 10° C. The precipitate was collected by filtration and triturated with propan-2-ol/ether (1:1) to give a solid which was dried under vacuum at 40° C. for 6.5 hours to give 2-cyclopentylamino-4'-phenoxyacetophenone hydrochloride.

c) The product from b) (35.1 g) was added to a solution of malononitrile (9.5 g) in methanol (500 ml) under nitrogen and then an aqueous solution of potassium hydroxide (17.0 g) in water (75 ml) was added dropwise over 30 minutes while keeping the temperature between 0 and 5° C. The mixture was then boiled under reflux for 2.5 hours. Further malononitrile (1.0 g) in methanol (10 ml) was added and the mixture boiled under reflux for a further 3 hours. The mixture was left to stand at ambient temperature for 18 hours and then the methanol was removed under reduced pressure and the residue kept under nitrogen. The residue was dissolved in dichloromethane (600 ml) and washed with water then brine and then dried, filtered and evaporated to give a brown solid which was triturated with diethyl ether to give 2-amino-3-cyano-1-cyclopentyl-4-(4-phenoxyphenyl)pyrrole which was used directly in the next part of this example.

d) The product from c) (25.9 g) was dissolved in a mixture of formamide (155 ml), N,N-dimethylformamide (52 ml) and formic acid (20.2 ml) and the mixture was heated under nitrogen at an internal temperature of 166° C. for four hours. The mixture was cooled and poured into water (3.5 l) and then extracted with ethyl acetate (3×1500 ml). The combined ethyl acetate extracts were washed with water, dried, filtered and evaporated to give a solid which was triturated with ether and filtered to give a solid which was recrystallised from industrial methylated spirit to give 7-cyclopentyl- 5-(4-phenoxyphenyl)-7H-pyrrolo[2,3-d]pyrimidin-4-ylamine, m.p. 178–179° C.

EXAMPLE 4

This Example was carried out in a similar manner to Example 2. 2-Bromo-4'-phenylacetophenone (25.0 g) in acetonitrile (150 ml) was reacted with tert-butylamine (28.4 ml) to give 4'-phenyl-2-(tert-butylamino)acetophenone hydrobromide (5.31 g) m.p. 234–237° C. (with decomposition). This compound was reacted with malononitrile (1.7 g) and potassium hydroxide (3.0 g) in water (4 ml) in methanol (100 ml) under nitrogen to give 2-amino-4-(4-biphenylyl)-3-cyano-1-(tert-butyl)pyrrole (3.75 g) which was suspended in formamide (200 ml) saturated with ammonia and then the mixture was heated at 200–205° C. for two hours whilst ammonia was being passed through the mixture. After cooling the mixture was added to ice-water (600 g) under nitrogen and the solid collected by filtration, purified by flash column chromatography on silica using ethyl acetate/triethylamine (19:1) as the mobile phase to give 5-(4-biphenylyl)-7-tert-butyl-7H-pyrrolo[2,3-d]pyrimidin-4-ylamine, m.p. 212–214° C.

EXAMPLE 5

This Example was carried out in a similar manner to Example 2. Neopentylamine (18.4 g) in toluene (100 ml) was reacted with 2-bromo-4'-phenoxyacetophenone (33.0 g) in toluene (150 ml) to give 2-neopentyl-4'-phenoxyacetophenone hydrochloride (13.6 g) which was reacted with potassium hydroxide (7.3 g) in water (10 ml) and malononitrile (3.2 g) in methanol (200 ml) under nitrogen to give 2-amino-3-cyano-1-neopentyl-4-(4-phenoxyphenyl)pyrrole (6.9 g) which was dissolved in formamide (250 ml) saturated with ammonia and reacted to give a crude product which was purified by flash column chromatography on silica using ethyl acetate/triethylamine (19:1) as the mobile phase to give a mixture of the desired product and 4-amino-5-[4-(4-bromophenoxy)phenyl]-7-neopentylpyrrolo[2,3-d]pyrimidine. This mixture was purified by hydrogenating the crude product (1.15 g) in propan-1-ol (40 ml), ammonium formate (1.1 g) and 10% palladium on charcoal (0.3 g) with stirring under nitrogen. The mixture was filtered. The filtrate was concentrated under reduced pressure to give a residue which was taken up in warm methanol and then cooled and water added to induce crystallisation. The mixture was cooled and the solid collected by filtration and dried to give 7-neopentyl-5-(4-phenoxyphenyl)-7H-pyrrolo[2,3-d]pyrimidin-4-ylamine, m.p. 158–158.5° C.

EXAMPLE 6

This Example was carried out in a similar manner to Example 2. 2-Bromo-4'-phenylthioacetophenone (159.0 g), propan-2-ol (400 ml) and tert-butylamine (100 ml) was boiled under reflux for 18 hours under nitrogen to give 4'-phenylthio-2-(tert-butylamino)acetophenone hydrochloride (74.0 g) which was reacted with malononitrile (21.63 g) in methanol (2000 ml) and potassium hydroxide (0.668 mol) to give 2-amino-3-cyano-4-(4-phenylthiophenyl)-1-(tert-butyl)pyrrole (33.44 g) which was dissolved in formamide (1100 ml) and heated to 170–180° C. for two hours with ammonia gas bubbling through the reaction mixture to give 7-tert-butyl-5-(4-phenylthiophenyl)-7H-pyrrolo[2,3-d]-pyrimidin-4-ylamine, m.p. 151.5–152.5° C.

EXAMPLE 7

This Example was carried out in a similar manner to Example 3. 4-(4-Methoxyphenoxy)acetophenone (50.8 g) was reacted with pyridinium tribromide (67.0 g) in acetic acid (650 ml) to give 2-bromo-4'-(4-methoxyphenoxy) acetophenone (80.0 g) which was reacted with tert-butylamine (70 ml) in propan-2-ol (250 ml) to give 2-(tert-butyl)4'-(4-methoxyphenoxy)acetophenone hydrochloride (33.3 g) which was dissolved in methanol (475 ml) and reacted with malononitrile (9.5 g) and potassium hydroxide (16.6 g) to give 2-amino-3-cyano-4-(4-methoxyphenoxyphenyl)-1-(tert-butyl)pyrrole. This material (20.0 g) was dissolved in formamide (650 ml) and ammonia was bubbled through while the mixture was heated at 190° C. for two hours to give, on work up and flash column chromatrography on silica using ethyl acetate/triethylamine (19:1) as the mobile phase, 7-tert-butyl-5-[4-(4-methoxyphenoxy)phenyl]-7H-pyrrolo[2,3-d]pyrimidin-4-ylamine, m.p. 171–172° C.

EXAMPLE 8 a) In a similar manner to Example 10 b), 4-chloro-5-iodo-7-isopropylpyrrolo-[2,3-d]pyrimidine (0.57 g), was reacted with 4-nitrophenylboronic acid (0.30 g) using bis (triphenylphosphine)palladium (II) chloride (0.126 g) to give 4-chloro-7-isopropyl-5-(4-nitrophenyl)pyrrolo[2,3-d] pyrimidine which was reduced using a mixture of ammonium chloride (22 mg),iron powder (0.45 g) in water (2 ml) and industrial methylated spirit (10 ml) to give 4-chloro-5-(4-aminophenyl)-7-isopropylpyrrolo[2,3-d]pyrimidine which was reacted with ammonia in 1,4-dioxen in a sealed vessel to give 4-amino-5-(4-aminophenyl)-7-isopropyl-pyrrolo[2,3-d]pyrimidine.

b) Benzoyl chloride (101 mg) in dichloromethane (1.0 ml) was added to a mixture of 4-amino-5-(4-aminophenyl)-7-isopropylpyrrolo[2,3-d]pyrimidine (175 mg), in dichloromethane (7 ml) and triethylamine (73 mg) at 0° C. under nitrogen with stirring. The mixture was stirred at 0° C. for four hours and then allowed to warm up to ambient temperature over one hour. The reaction mixture was stirred at ambient temperature for 18 hours and then quenched by the addition of saturated sodium bicarbonate solution (10 ml) with ice-cooling. The organic layer was separated and the aqueous layer was extracted with ethyl acetate (3×20 ml). The combined organic layers were washed with water, dried and evaporated to give a pale yellow solid which was purified by preparative HPLC to give N-(4-{4-amino-7-isopropyl-7H-pyrrolo[2,3-d]pyrimidin-5-yl}phenyl)-benzamide, m.p. 192–195° C.

EXAMPLE 9 a) A solution of tert-butylamine (154 ml) in acetonitrile (100 ml) was added over 10 minutes to a solution of 2-chloro-4'-iodoacetophenone (158.0 g, prepared as described in Organic Magnetic Resonance 12 (12), 1979 pages 691–695) in acetonitrile (700 ml) with stirring under nitrogen at 20° C. The mixture was warmed to 30° C. whereupon a solution was formed, then a slight exotherm occurred and tert-butylamine hydrochloride precipitated. The mixture was kept below 37° C. by occasional cooling. The mixture was left stirring at ambient temperature for 18 hours then filtered and the residue washed with acetonitrile. The combined filtrate and washings were reduced in volume and then taken up in a mixture of ether (700 ml) and water (500 ml). The mixture was stirred while the pH was adjusted to 9 using dilute hydrochloric acid. The mixture was filtered to remove tert-butylamine hydrochloride. The filtrate was acidified with dilute hydrochloric acid to give 4'-iodo-2-(tert-butylamino)acetophenone hydrochloride (102.0 g).

This product was reacted with malononitrile (29.9 g) and potassium hydroxide (52.3 g) in methanol (1.5 l) and water (100 ml) in a similar manner to Example 2, to give 2-amino-3-cyano-4-(4-iodophenyl)-1-(tert-butyl)pyrrole (63.2 g), m.p. 166.5–167° C.

b) The product from a) was reacted with formamide (2 l) whilst ammonia was being passed through the solution in a similar manner to Example 2, to give a crude solid which was recrystallised from toluene to give 4-amino-5-(4-iodophenyl)-7-(tert-butyl)pyrrolo[2,3-d]pyrimidine, m.p. 188–189° C.

c) The product (600 mg) from b), 4-acetamidophenol (828 mg), potassium carbonate (702 mg), copper (I) chloride (60 mg), 8-hydroxyquinoline (96 mg) and dimethylacetamide (15 ml) was stirred and boiled under reflux under nitrogen for four hours. The mixture was diluted with water (100 ml) and ethyl acetate (50 ml), basified with 5M sodium hydroxide solution (1 ml) and filtered. The filtrate was separated and the organic layer was washed with water, dried and evaporated to give a residue which was purified by flash column chromatography on silica using ethyl acetate as the mobile phase to give N-{4-[4-(4-amino-7-tert-butyl-7H-pyrrolo[2,3-d]pyrimidin-5-yl)phenoxy]phenyl}-acetamide. This structure was confirmed by $^1$H nmr.

EXAMPLE 10 a) 4-Chloro-5-iodopyrrolo[2,3-d]pyrimidine (10.0 g, see Example 17) was added in portions with stirring under nitrogen at 0° C. to a suspension of sodium hydride (1.6 g of a 60% dispersion in mineral oil) in N,N-dimethylformamide (250 ml). When the addition was complete the mixture was allowed to warm up to ambient temperature and when no more gas evolution was observed, a solution of isopropyl bromide (34.0 ml) in N,N-dimethylformamide (20 ml) was added dropwise. The mixture was stirred at ambient temperature overnight then quenched by the dropwise addition of water (300 ml) with external ice-cooling. The mixture was then washed with ethyl acetate (3×300 ml), the combined organic layers were washed with water, dried, filtered and evaporated to give 4-chloro-5-iodo-7-isopropylpyrrolo-[2,3-d]pyrimidine as a yellow solid, m.p. 116–118° C. The structure was confirmed by $^1$H nmr.

b) A mixture of 4-chloro-5-iodo-7-isopropylpyrrolo[2,3-d]pyrimidine (2.8 g), 4-methoxybenzeneboronic acid (1.32 g), bis(triphenylphosphine)palladium (II) chloride (625 mg), toluene (85 ml), ethanol (11 ml), water (22 ml) and sodium bicarbonate (2.2 g) was heated under nitrogen at 105° C. for 18 hours. The mixture was allowed to cool to ambient temperature and then partitioned between ethyl acetate (100 ml) and brine (100 ml). The organic layer was separated and the aqueous layer was washed with ethyl acetate (2×50 ml). The combined organic layers were washed with water, dried, filtered and evaporated under reduced pressure to give a black oil which solidified on cooling. This material was purified by flash column chromatography on silica using cyclohexane/ethyl acetate (7:3) as the mobile phase. Appropriate fractions were combined and concentrated under reduced pressure to give a yellow oil which solidified on standing to give 4-chloro-7-isopropyl-5-(4-methoxyphenyl) pyrrolo[2,3-d]pyrimidine. The structure was confirmed by $^1$H nmr.

c) A mixture of 4-chloro-7-isopropyl-5-(4-methoxyphenyl)pyrrolo-[2,3-d]pyrimidine (1.6 g), concentrated ammonia (80 ml, S.G. 0.880) and 1,4-dioxane (80 ml) was heated in a pressure vessel at 120° C. for 18 hours. The mixture was cooled to ambient temperature and the solvent was removed under reduced pressure to give a solid residue which was partitioned between ethyl acetate (100 ml) and water (100 ml). The aqueous layer was extracted with ethyl acetate and the combined organic layers were washed with water, dried, filtered and evaporated to give 4-amino-7-isopropyl-5-(4-methoxyphenyl)pyrrolo[2,3-d]-pyrimidine. The structure was confirmed by $^1$H nmr.

d) A solution of boron tribromide (14.4 ml of a 1M solution in dichloromethane) was added dropwise to a stirred solution of 4-amino-7-isopropyl-5-(4-methoxyphenyl) pyrrolo[2,3-d]pyrimidine (1.35 g) in dichloromethane (100 ml) at −10° C. under nitrogen. The reaction mixture was allowed to warm to 0° C. and stirred at this temperature for one hour. Additional boron tribromide (9.6 ml of a 1M solution in dichloromethane) was added at −10° C. and the mixture was allowed to warm to 0° C. and stirred for a further hour. The reaction mixture was quenched by the dropwise addition of saturated sodium bicarbonate solution (50 ml). The mixture was allowed to stand overnight and the dichloromethane layer separated off. Insoluble material at the interface was removed by filtration and dried to yield 4-amino-5-(4-hydroxyphenyl)-7-isopropylpyrrolo-[2,3-d]pyrimidine. The structure was confirmed by $^1$H nmr.

e) A mixture of 4-amino-5-(4-hydroxyphenyl)-7-isopropylpyrrolo[2,3-d]-pyrimidine (0.29 g), 2-fluoronitrobenzene (0.15 g), potassium carbonate (0.149 g) and N,N-dimethylformamide (4.0 ml) was shaken and heated at 120° C. for 5 hours. The mixture was evaporated to dryness under reduced pressure and the residue was partitioned between ethyl acetate (30 ml) and water (20 ml). The organic layer was separated, washed with water, and then with dilute sodium hydroxide solution, and then with brine, then dried, filtered and evaporated to give a solid which was triturated with ether to give 7-isopropyl-5-[4-(2-nitrophenoxy)phenyl]-7H-pyrrolo[2,3-d]pyrimidin-4-ylamine. The structure was confirmed by $^1$H nmr.

EXAMPLE 11

A mixture of 7-isopropyl-5-[4-(2-nitrophenoxy)phenyl]-7H-pyrrolo[2,3-d]-pyrimidin-4-ylamine (0.15 g), ammonium formate (3 equivalents), 10% palladium on charcoal (15 mg) and ethanol (5 ml) was boiled under reflux under nitrogen for 2 hours. Further ammonium formate (100 mg) was added after one hour. The mixture was cooled and filtered through silica. The filter bed was washed with industrial methylated spirit (2×10 ml). The filtrate was evaporated and the residue was extracted with ethyl acetate. The ethyl acetate was removed under reduced pressure to give a residue which was purified by flash column chromatography on silica using ethyl acetate as the mobile phase to give 5-[4-(2-aminophenoxy)phenyl]-7-isopropyl-7H-pyrrolo[2,3-d]-pyrimidin-4-ylamine. The structure was confirmed by $^1$H nmr.

EXAMPLE 12

Triethylamine (56 mg) was added to a solution of give 4-amino-5-[4-(2-aminophenoxy)phenyl]-7-isopropylpyrrolo[2,3-d]pyrimidine (67 mg) in dry acetonitrile (5.0 ml) followed by acetyl chloride (14.6 mg). The mixture was stirred at ambient temperature for one hour and then further acetyl chloride (7.3 mg) in acetonitrile (0.25 ml) was added and the mixture stirred at ambient temperature for 0.5 hours. The mixture was evaporated to dryness under reduced pressure and the residue was partitioned between water (2 ml) and dichloromethane (2 ml). The mixture was filtered through an Empore® cartridge which was washed with dichloromethane (2 ml). The dichloromethane layer was separated and evaporated to give N-{2-[4-(4-amino-(7-isopropyl-7H-pyrrolo[2,3-d]pyrimidin-5-yl)phenoxy]phenyl}acetamide. The structure was confirmed by $^1$H nmr.

EXAMPLE 13

A mixture of N-{4-[4-(4-amino-7-tert-butylpyrrolo[2,3-d]pyrimidin-5-yl)phenoxy]-phenyl}acetamide (1.8 g), prepared as described in Example 9, industrial methylated spirit (5 ml) and hydrazine hydrate (30 ml) was boiled under reflux for 36 hours. The reaction mixture was cooled to ambient temperature, diluted with water (100 ml) and the mixture extracted with ethyl acetate (3×50 ml) to give 5-[4-(4-amino-phenoxy)phenyl]-7-tert-butyl-7H-pyrrolo[2,3-d]pyrimidin-4-ylamine. The structure was confirmed by $^1$H nmr.

EXAMPLE 14

In a similar manner to Example 9, 4-amino-5-(4-iodophenyl)-7-tert-butyl-pyrrolo[2,3-d]pyrimidine (1.8 g), 3-acetamidophenol (2.48 g), potassium carbonate (2.1 g), copper (I) chloride (0.09 g), 8-hydroxyquinoline (0.15 g) and dimethyl-acetamide (40 ml) were stirred and heated at 180° C. under nitrogen for 4 hours to give N-{3-[4-(4-amino-(7-tert-butyl-7H-pyrrolo[2,3-d]-pyrimidin-5-yl)phenoxy]phenyl}-acetamide. This structure was confirmed by $^1$H nmr.

EXAMPLE 15

A mixture of N-{3-[4-(4-amino-(7-tert-butyl-7H-pyrrolo[2,3-d]-pyrimidin-5-yl)phenoxy]-phenyl}acetamide (0.6 g), hydrazine hydrate (5 ml) and industrial methylated spirit (2 ml) was heated on a steam bath for two days and then worked up as described in Example 14 to give a residue which was purified by flash column chromatography on silica gel using ethyl acetate as the mobile phase to give 4-amino-5-[4-(3-aminophenoxy)phenyl]-7-tert-butyl-7H-pyrrolo[2,3-d]pyrimidin-4-ylamine. This structure was confirmed by $^1$H nmr.

EXAMPLE 16

In a similar manner to Example 9, a mixture of 4-amino-5-(4-iodophenyl)-7-(tert-butyl)pyrrolo[2,3-d]pyrimidine (100 mg), potassium carbonate (104 mg), N-methyl-(4-acetamido)phenol (120 mg), 8-hydroxyquinoline (8 mg), copper (I) chloride (5 mg) and dimethylacetamide (8 ml) gave N-{4-[4-(4-amino-7-tert-butylpyrrolo[2,3-d]-pyrimidin-5-yl)phenoxy]phenyl}-N-methylacetamide. This structure was confirmed by $^1$H nmr.

EXAMPLE 17 a) Iodine (52.9 g) was added to a stirred solution of 4-chloro-pyrrolo[2,3-d]-pyrimidine (29.1 g, J. Chem. Soc. 1960, 131) in N,N-dimethylformamide (400 ml). Potassium hydroxide pellets (31.9 g) were added in portions to the cooled mixture so that the temperature of the reaction mixture was maintained around 20° C. and this mixture was stirred at ambient temperature for 2 hours. A solution of sodium thiosulphate (900 ml of a 10% aqueous solution) was added in a steady stream keeping the temperature at 30° C. by external cooling. The mixture was extracted with ethyl acetate and the combined extracts were dried, filtered and evaporated under reduced pressure to give a residue which was added to water (1 L) and extracted with ethyl acetate (2×150 ml). The combined ethyl acetate extracts were dried and evaporated to give a solid which was recrystallised from ethyl acetate. The solid obtained was stirred with methanol (800 ml) and filtered to remove some insoluble material. The filtrate was evaporated to dryness to give a pale yellow solid which was identified as 4-chloro-5-iodo-pyrrolo[2,3-d]-pyrimidine, m.p. 219–221° C.

b) 4-Chloro-5-iodo-pyrrolo[2,3-d]-pyrimidine (5.0 g) was added under nitrogen to a mixture of sodium hydride (0.8 g of a 60% dispersion in mineral oil) in N,N-dimethylformamide (100 ml) at 0° C. and then the mixture was allowed to warm to ambient temperature. When hydrogen evolution had ceased a solution of isopropyl bromide (17 ml) in N,N-dimethylformamide (50 ml) was added dropwise. The mixture was stirred for 20 hours at ambient temperature and then quenched with water (150 ml). The mixture was extracted with ethyl acetate to give 4-chloro-5-iodo-7-isopropylpyrrolo[2,3-d]pyrimidine.

c) A mixture of 4-chloro-5-iodo-7-isopropylpyrrolo[2,3-d]pyrimidine (0.57 g), 4-nitrophenylboronic acid (0.30 g), bis(triphenylphosphine)palladium (II) chloride (0.126 g), toluene (15 ml), ethanol (2 ml), water (4 ml) and sodium bicarbonate (0.45 g) was heated under nitrogen at 105° C. for 8 hours. The mixture was cooled to ambient temperature and then partitioned between brine (50 ml) and ethyl acetate (50 ml). The aqueous layer was further extracted with ethyl acetate and the combined ethyl acetate extracts were washed with water, dried, filtered and evaporated to leave a solid which was purified by flash column chromatography on silica using cyclohexane with increasing amounts of ethyl acetate as the mobile phase to give 4-chloro-7-isopropyl-5-(4-nitrophenyl)pyrrolo[2,3-d]pyrimidine.

d) A mixture of 4-chloro-7-isopropyl-5-(4-nitrophenyl)pyrrolo[2,3-d]pyrimidine (1.0 g), iron powder (1.76 g), ammonium chloride (86 mg), water (8 ml) and industrial methylated spirit (40 ml) was boiled under reflux for one hour. The mixture was filtered and the solvent evaporated. The residue was taken up in ethyl acetate and washed with water. The ethyl acetate extract was dried, filtered and evaporated to give 5-(4-aminophenyl)-4-chloro-7-isopropylpyrrolo[2,3-d]pyrimidine.

e) Benzenesulphonyl chloride (0.27 g) in dichloromethane (5 ml) was added dropwise with stirring to a solution of 5-(4-aminophenyl)-4-chloro-7-isopropylpyrrolo[2,3-d]pyrimidine (0.40 g) and triethylamine (155 mg) in dichloromethane (15 ml) at 0° C. under nitrogen. The mixture was stirred at 0° C. for one hour and then warmed to ambient temperature and stirred at this temperature for 18 hours. Water (20 ml) was added and the mixture was extracted with dichloromethane. The combined organic layers were washed with sodium bicarbonate, dried, filtered and evaporated to give N-[4-(4-chloro-7-isopropylpyrrolo[2,3-d]pyrimidin-5-yl)phenyl]benzenesulphonamide f) A mixture of N-[4-(4-chloro-7-isopropylpyrrolo[2,3-d]pyrimidin-5-yl)phenyl]-benzenesulphonamide (0.34 g), concentrated ammonia (30 ml, SG 0.880) and 1,4-dioxane (30 ml) was heated with stirring at 120° C. in a pressure vessel for 16 hours. The mixture was allowed to cool to ambient temperature and the solvent was removed under reduced pressure to give a residue which was partitioned between water (40 ml) and ethyl acetate (40 ml). The organic layer was separated and the aqueous layer was further extracted with ethyl acetate (2×40 ml). The combined ethyl acetate extracts were washed, dried, filtered and evaporated to give a solid which was purified by flash column chromatography on silica using ethyl acetate/cyclohexane (8:2) as the mobile phase. Appropriate fractions were collected, combined and concentrated to give N-[4-(4-amino-7-isopropyl-7H-pyrrolo[2,3-d]pyrimidin-5-yl)phenyl] benzenesulphonamide, m.p. 238–240° C.

EXAMPLE 18

A mixture of 4-amino-5-(4-phenoxyphenyl)-7-(tert-butyl) pyrrolo[2,3-d]-pyrimidine (0.20 g), N-chlorosuccinimide (80 mg) and dichloromethane (5 ml) was stirred at ambient temperature for 18 hours. The mixture was concentrated under reduced pressure and the residue was partitioned between ethyl acetate and water. The organic layer was separated, dried and evaporated to give an oil which was purified by flash column chromatography on silica using ethyl acetate/triethylamine (95:5) as the mobile phase. Appropriate fractions were collected, combined and evaporated to give 7-(tert-butyl)-6-chloro-5-(4-phenoxyphenyl)-7H-pyrrolo-[2,3-d]pyrimidin-4-ylamine, m.p. 136.8–137.8° C.

EXAMPLE 19

A solution of sodium periodate (0.60 g) dissolved in water (16 ml) was added to a solution of 4-amino-5-[4-(phenylthio)phenyl]-7-(tert-butyl)pyrrolo[2,3-d]pyrimidine (1.0 g) in glacial acetic acid (30 ml) with stirring whilst keeping the temperature below 5° C. The mixture was stirred for 66 hours at ambient temperature. The mixture was filtered and the filtrate was added to water (300 ml). This mixture was basified with solid sodium bicarbonate, filtered to remove a small amount of solid which was discarded and the filtrate extracted with ethyl acetate to give a residue which was purified by flash column chromatography on silica using ethyl acetate/triethylamine (9:1) as the mobile phase, to give a solid which was rechromatographed under the same conditions to give 7-tert-butyl-5-(4-phenylsulphinylphenyl)-7H-pyrrolo[2,3-d]pyrimidin-4-ylamine, m.p. 180–182° C.

EXAMPLE 20

A solution of potassium peroxymonosulphate (4.93g) in water (10 ml) was added dropwise with stirring to a solution of 4-amino-5-[4-(phenylthio)phenyl]-7-(tert-butyl)pyrrolo[2,3-d]pyrimidine (1.0 g) in methanol (5 ml) and glacial acetic acid (5 ml) keeping the temperature below 5° C. The mixture was then stirred at ambient temperature for 3 hours and then diluted with water (50 ml). The mixture was extracted with ethyl acetate to give a solid which was purified by flash column chromatography on silica using ethyl acetate/triethylamine (9:1) as the mobile phase. Appropriate fractions were combined and concentrated to give a solid which was triturated with petroleum ether, boiling point 60–80° C. to give 7-tert-butyl-5-(4-phenylsulphonylphenyl)-7H-pyrrolo[2,3-d]pyrimidin-4-ylamine, m.p. 222–224° C.

EXAMPLES 21a and 21b

A mixture of 7-(tert-butyl)-4-amino-5-[4-(4-methoxyphenoxy)phenyl]-7H-pyrrolo-[2,3-d]pyrimidin-4-ylamine (1.1 g, Example 7), glacial acetic acid (25 ml) and aqueous hydrobromic acid (25 ml) of a 48% w/v solution was boiled under reflux for 1 hour. The mixture was allowed to cool to ambient temperature and then added to ice-water and ethyl acetate. This mixture was stirred while excess solid sodium bicarbonate was added slowly. The ethyl acetate layer was separated off, washed with water, dried and evaporated to give a solid residue which is purified by flash column chromatography on silica using ethyl acetate/triethylamine (19:1) as the mobile phase with an increasing amount of methanol. Appropriate fractions were collected, combined and evaporated to give 4-[4-(4-amino-7-tert-butyl-7H-pyrrolopyrimidin-5-yl)-phenoxy]phenol, m.p. 254–255° C. (Example 21 a) and 4-[4-(4-amino-7H-pyrrolo[2,3-d]-pyrimidin-5-yl)phenoxy]phenol, m.p. 304–305° C. (Example 21b).

EXAMPLE 22

A mixture of 5-(4-phenoxyphenyl)-7H-pyrrolo[2,3-d] pyrimidin-4-ylamine (0.50 g), ethylene carbonate (0.16 g), N,N-dimethylformamide (20 ml) and a catalytic amount of sodium hydroxide powder was boiled under reflux for 1 hour. The mixture was evaporated under reduced pressure and the residue was triturated with water (30 ml). The mixture was filtered to give a solid which was purified by flash column chromatography on silica using ethyl acetate/industrial methylated spirit (9:1) as the mobile phase to give 2-[4-amino-5-(4-phenoxyphenyl)-7H-pyrrolo[2,3-d]pyrimidin-7-yl]ethanol, m.p. 144.5–145° C.

EXAMPLE 23

Sodium hydride (60 mg of a 60% dispersion in mineral oil) was added to a solution of 5-(4-phenoxyphenyl)-7H-pyrrolo[2,3-d]pyrimidin-4-ylamine (302 mg) in dry N,N-dimethylformamide (20 ml) with stirring under nitrogen at ambient temperature. The mixture was stirred for 30 minutes at ambient temperature and then cyclopentene oxide (200 mg) was added and the mixture heated at 150° C. for 3 hours and then at 170° C. for 1 hour. The mixture was concentrated under reduced pressure and the residue was triturated with water and filtered to give a solid. This solid was purified by flash column chromatography on silica using ethyl acetate/industrial methylated spirit (9:1) as the mobile phase to give 2-[4-amino-5-(4-phenoxyphenyl)-7H-pyrrolo[2,3-d]pyrimidin-7-yl]cyclopentanol, m.p. 162–162.5° C. (after recrystallisation from methanol/water).

EXAMPLE 24

A mixture of 5-(4-phenoxyphenyl)-7H-pyrrolo[2,3-d]pyrimidin-4-ylamine (600 mg) and tetrakis (triphenylphosphine) palladium (40 ml) and dry dimethyl sulphoxide (30 ml) was stirred under nitrogen in an ice/water bath and then a solution of cyclopentadiene monoepoxide (200 mg) in tetrahydrofuran (10 ml) was added via syringe under nitrogen at 0° C. The mixture was stirred at ambient temperature for 66 hours and then the tetrahydrofuran was removed under reduced pressure and water was added to the residue. The mixture was allowed to stand for 18 hours and then extracted with ethyl acetate to give a residue which was purified by flash column chromatography on silica using ethyl acetate/industrial methylated spirit (9:1) as the mobile phase to give 4-[4-amino-5-(4-phenoxyphenyl)-7H-pyrrolo[2,3-d]pyrimidin-7-yl] cyclopent-2-enol, as an oil. The structure was confirmed by [1]Hnmr and mass spectra.

EXAMPLE 25

4-[4-Amino-5-(4-phenoxyphenyl)-7H-pyrrolo[2,3-d] pyrimidin-7-yl]cyclopent-2-enol (110 mg) was hydrogenated in ethanol (20 ml) with gaseous hydrogen at atmospheric pressure using 10% palladium on charcoal (50 mg) as the catalyst. The catalyst was removed by filtration and the filtrate was evaporated to give 3-[4-amino-5-(4-phenoxyphenyl)-7H-pyrrolo[2,3-d]pyrimidin-7-yl]cyclopentanol, as an oil. The structure was confirmed by $^1$H nmr and mass spectra.

EXAMPLE 26

A mixture of 4-[4-amino-5-(4-phenoxyphenyl)-7H-pyrrolo[2,3-d]pyrimidin-7-yl]cyclopent-2-enol (188 mg), 4-methylmorpholine-N-oxide (63 mg) in tetrahydrofuran (5 ml) was stirred at ambient temperature for 10 minutes. Osmium tetroxide (0.42 ml of a 2.5% w/v solution in tert-butanol) was added to the mixture. The mixture was stirred at ambient temperature for 3 hours and then chromatographed directly using flash column chromatography on silica using ethyl acetate/industrial methylated spirit (9:1) as the mobile phase to give 4-[4-amino-5-(4-phenoxyphenyl)-7H-pyrrolo[2,3-d]pyrimidin-7-yl]cyclopentan-1,2,3-triol, as an oil. The structure was confirmed by $^1$H nmr and mass spectra.

EXAMPLE 27 a) A mixture of 4-chloro-7-cyclopentyl-5-iodopyrrolo[2,3-d]pyrimidine (1.26 g) and potassium (2-phenoxyphenyl)trifluoroborate (1.0 g, prepared by reacting 2-phenoxybromobenzene with butyllithium in tetrahydrofuran at −70° C. followed by triisopropyl borate (IV) followed by potassium hydrogen fluoride by a method analogous to that described in J. Org. Chem. 1995, 60, 3020–3027), in degassed toluene (40 ml), ethanol (10 ml) and water (10 ml) was stirred under nitrogen and bis(triphenylphosphine) palladium (II) chloride (0.25 g) was added followed by sodium bicarbonate (2.0 g). The mixture was stirred and heated at 105° C. for 16 hours and then cooled to ambient temperature. The mixture was separated and the upper layer was evaporated under reduced pressure to give a residue which was purified by flash column chromatography on silica using petroleum ether/ether (2:1) as a mobile phase to give 4-chloro-7-cyclopentyl-5 -(2-phenoxyphenyl)pyrrolo[2,3-d]pyrimidine which was used directly in the next part of this example.

b) A mixture of the product from a) above (0.79 g), 1,4-dioxane (60 ml) and concentrated aqueous ammonia solution (60 ml, S.G. 0.880) was stirred and heated at 120° C. for 18 hours in a pressure vessel. The mixture was evaporated under reduced pressure and the residue was partitioned between water and ethyl acetate. The organic layer was separated, dried and evaporated to give a gum which was crystallised from methanol to give 7-cyclopentyl-5-(2-phenoxyphenyl)-7H-pyrrolo[2,3-d]pyrimidin-4-ylamine, m.p. 109–110° C.

EXAMPLE 28

This example was carried out in a similar manner to Example 27, except that the initial starting material was 3-phenoxybromobenzene to give 4-cyclopentyl-5-(3-phenoxyphenyl)-7H-pyrrolo[2,3-d]pyrimidin-4-ylamine, m.p. 127.5–128° C.

EXAMPLE 29 a) 2-Phenyl-1,3-dioxan-3-ol (4.89 g) in dry pyridine (20 ml) was stirred at 0–2° C. whilst a solution of freshly purified 4-toluenesulphonyl chloride (5.9 g) in dry pyridine (80 ml) was added dropwise with stirring, whilst keeping the temperature below 2° C. The mixture was stirred for 100 minutes at 2° C. and then added to water (500 ml). The liquid was decanted off and the residual gum was dissolved in ether, dried and evaporated to give a residue which was crystallised from methanol to give 2-phenyl-1,3-dioxan-3-yl-4-toluene sulphonate, m.p. 125.3–125.9° C.

b) A mixture of sodium hydride 4-amino-5-(4-phenoxyphenyl)-7H-pyrrolo[2,3-d]-pyrimidine hydrobromide (0.6 g), sodium hydride (80 mg of a 60% dispersion in mineral oil) and dry N,N-dimethylformamide (30 ml) was stirred under nitrogen for 30 minutes. The 4-toluene sulphonate from a) (0.76 g) was added and the mixture was heated at 145° C. for 16 hours. The solvent was removed under reduced pressure and water was added to the residue. The mixture was filtered to give a solid which was purified by flash column chromatography using ethyl acetate/industrial methylated spirit (9:1) as the mobile phase to give 5-(4-phenoxyphenyl)-7-(2-phenyl-1,3-dioxan-5-yl)-7H-pyrrolo[2,3-d]pyrimidin-4-ylamine. The structure was confirmed by $^1$H nmr and mass spectra.

EXAMPLE 30

Dilute hydrochloric acid (45 ml of 2M solution) was added to 5-(4-phenoxyphenyl)-7-(2-phenyl-1,3-dioxan-5-yl)-7H-pyrrolo[2,3-d]pyrimidin-4-ylamine (170 mg) and the mixture heated to boiling under reflux. Propan-1-ol (30 ml) was added and the mixture boiled under reflux for 6 hours and then the propanol was distilled off. The mixture was evaporated under reduced pressure to give a residue which was triturated with ethyl acetate and then filtered to give a solid which was dissolved in methanol, and purified by chromatography to give 2-[4-amino-5-(4-phenoxyphenyl)-7H-pyrrolo[2,3-d]pyrimidin-7-yl]propan-1,3-diol. The structure was confirmed by $^1$H nmr and mass spectra.

EXAMPLE 31 a) Sodium hydride (0.28 g of 60% dispersion in mineral oil) was added to a solution of 4-chloro-5-iodo-7H-pyrrolo[2,3-d]pyrimidine (1.96 g) in dry N,N-dimethylformamide (40 ml) with stirring under nitrogen at ambient temperature. The mixture was then stirred for 30 minutes and allyl bromide (0.62 ml) was added dropwise. After stirring for 1 hour at ambient temperature more allyl bromide (0.20 ml) was added and the mixture was left stirring at ambient temperature for 18 hours. The mixture was added to water with stirring and the solid which precipitated was collected by filtration and dried to give 4-chloro-5-iodo-7-(prop-1-en-3-yl)-7H-pyrrolo[2,3-d]-pyrimidine which was used directly in b).

b) The product from a) (2.05 g) was dissolved in tetrahydrofuran (50 ml) and stirred at ambient temperature with 4-methylmorpholine N-oxide (850 mg) and then a solution of osmium tetroxide in tert-butanol (5 ml of a 2.5% w/v solution) was added. The mixture was left standing for 18 hours, then evaporated under reduced pressure to give a solid which was dissolved in toluene/propan-2-ol (2:1) then hot filtered and the filtrate evaporated to give 3-[4-chloro-5-iodo-7H-pyrrolo[2,3-d]pyrimidin-7-yl]propan-1,2-diol.

c) A mixture of the product from b) (1.90 g), 4-phenoxyphenylboronic acid (1.14 g), degassed toluene (100 ml), degassed ethanol (25 ml), degassed water (25 ml) was stirred under nitrogen and then bis(triphenylphosphine) palladium (II) chloride (0.40 g) was added followed by sodium bicarbonate (2.0 g). The mixture was boiled under reflux with stirring for 18 hours. The mixture was worked up as described in Example 10b) to give an oil which was purified by flash column chromatography on silica using ethyl acetate/industrial methylated spirit (9:1) as the mobile phase to give 3-[4-chloro-5-(4-phenoxyphenyl)-7H-pyrrolo[2,3-d]pyrimidin-7-yl]propan-1,2-diol.

d) 3-[4-Chloro-5-(4-phenoxyphenyl)-7H-pyrrolo[2,3-d]pyrimidine-7-yl]propan-1,2-diol (0.6 g) was dissolved in 1,4-dioxane (60 ml) and concentrated aqueous ammonia (60 ml, S.G. 0.880) was added. The mixture was stirred and heated at 120° C. for 18 hours in a pressure vessel. The mixture was evaporated under reduced pressure to give a residue which was partitioned between water and ethyl acetate. The ethyl acetate layer was separated, washed with water, dried and evaporated to give a residue which was purified by flash column chromatography on silica using ethyl acetate/industrial methylated spirit (9:1) as the mobile phase to give 3-[4-amino-5-(4-phenoxyphenyl)-7H-pyrrolo[2,3-d]pyrimidin-7-yl]propan-1,2-diol. The structure was confirmed by $^1$H nmr and mass spectra.

EXAMPLE 32 a) In a similar manner to Example 17b 4-chloro-5-iodo-7H-pyrrolo[2,3-d]pyrimidine was reacted with sodium hydride in N,N-dimethylformamide at 0° C. and then with bromocyclopentane to give, after work-up, 4-chloro-7-cyclopentyl-5-iodopyrrolo[2,3-d]pyrimidine.

b) 2-Methoxyaniline was brominated with 2,4,4,6-tetrabromo-2,5-cyclohexadien-1-one to give 4-bromo-2-methoxyaniline which was reacted with di-tert-butyldicarbonate in tetrahydrofuran to protect the amine group. The product was treated with butyllithium at −78° C. and then with trimethyltin chloride to give 4-tert-butoxycarbonylamino-3-methoxyphenyl trimethyl stannane.

c) The product from a) (4.91 g) and the product from b) (5.45 g) were reacted together in the presence of triphenylarsine (1.07 g) and tris(dibenzylidene acetone)dipalladium (0) (0.65 g) in N,N-dimethylformamide (100 ml) at 65° C. with stirring under nitrogen for 18 hours. The mixture was cooled to ambient temperature then added to water. This mixture was extracted with ethyl acetate to give an oil which was purified by flash column chromatography on silica using cyclohexane/ethyl acetate (19:1) with gradually increasing amounts of ethyl acetate as the mobile phase to give 4-chloro-7-cyclopentyl-4-(4-tert-butoxycarbonylamino-3-methoxyphenyl)-pyrrolo[2,3-d]pyrimidine as a solid.

d) The product from c) (3.58 g) in dichloromethane (150 ml) was reacted with trifluoroacetic acid (15 ml) in dichloromethane (50 ml) at 0° C. to give, after work-up, 5-(4-amino-3-methoxyphenyl)-4-chloro-7-cyclopentylpyrrolo[2,3d]-pyrimidine as an oil.

e) The product from d) (0.5 g) was reacted with benzoyl chloride to give N-[4-(4-chloro-7-cyclopentyl-7H-pyrrolo[2,3-d]pyrimidin-5-yl)-2-methoxyphenyl]-benzamide after chromatography. The structure was confirmed by $^1$H nmr and mass spectra.

f) The product from e) (0.42 g) was reacted with concentrated aqueous ammonia (30 ml, S.G. 0.880) in 1,4-dioxane (30 ml) in a pressure vessel at 120° C. to give after work-up and chromatography N-[4-(4-amino-7-cyclopentyl-7H-pyrrolo[2,3-d]pyrimidin-5-yl)-2-methoxyphenyl]benzamide. The structure was confirmed by $^1$H nmr and mass spectra.

EXAMPLE 33

A solution of boron tribromide in dichloromethane (0.9 ml of a 1M solution) was added dropwise with stirring to a solution of the product from Example 32, N-[4-(4-amino-7-cyclopentyl-7H-pyrrolo[2,3-d]pyrimidin-5-yl)-2-methoxyphenyl]benzamide (130 mg) in dichloromethane (6 ml) at -10° C. under nitrogen, after the addition the reaction mixture was allowed to warm to 0° C. and stirred at 0° C. for 1.5 hours. The reaction mixture was quenched by the dropwise addition of saturated aqueous sodium bicarbonate solution (5 ml) at 0° C. There was an exotherm and the temperature of the mixture rose to 10° C. The mixture was allowed to warm to ambient temperature, then extracted with dichloromethane to give N-[4-(4-amino-7-cyclopentyl-7H-pyrrolo[2,3-d]pyrimidin-5-yl)-2-hydroxyphenyl] benzamide, m.p. 173–175° C. (with decomposition). The structure was confirmed by $^1$H nmr and mass spectra.

EXAMPLE 34

5-(4-Amino-3-methoxyphenyl)-4-chloro-7-cyclopentylpyrrolo[2,3-d]pyrimidine (0.50 g, prepared in a similar manner to Example 32) was reacted with benzenesulphonyl chloride (0.31 g) in pyridine (5 ml) and dichloromethane (1 ml) at 0° C. and the product obtained after work-up was reacted with ammonia in a similar manner to Example 32 to give N-[4-(4-amino-7-cyclopentyl-7H-pyrrolo[2,3-d]pyrimidin-5-yl)-2-methoxyphenyl] benzenesulphonamide, m.p. 113–115° C. The structure was confirmed by $^1$H nmr and mass spectra.

EXAMPLE 35

In a similar manner to Example 33, N-[4-(4-amino-7-cyclopentyl-7H-pyrrolo[2,3-d]pyrimidin-5-yl)-2-methoxyphenyl]benzenesulphonamide was reacted with boron tribromide in dichloromethane at −10° C. to give N-[4-(4-amino-7-cyclopentyl-7H-pyrrolo[2,3-d]pyrimidin-5-yl)-2-hydroxyphenyl]benzenesulphonamide, m.p. 265–267° C. The structure was confirmed by $^1$H nmr and mass spectra.

EXAMPLES 36a and 36b

N-[4-(4-Amino-7-cyclopentyl-7H-pyrrolo[2,3-d]pyrimidin-5-yl)-2-hydroxyphenyl]-4-tert-butylbenzenesulphonamide, m.p. 278–280° C. (Example 36a) was prepared in a similar manner to Examples 34 and 35 from N-[4-(4-amino-7-cyclopentyl-7H-pyrrolo[2,3-d]pyrimidin-5-yl)-2-methoxyphenyl]-4-tert-butylbenzenesulphonamide (Example 36b).

EXAMPLE 37 a) In a similar manner to Example 17 c) 4-chloro-5-iodo-7-cyclopentylpyrrolo-[2,3-d]pyrimidine (1.80 g) was reacted with 4-(2-methoxyphenoxy)phenyl-boronic acid to give 4-chloro-7-cyclopentyl-5-[4-(2-methoxy) phenoxyphenyl]-pyrrolo[2,3-d]pyrimidine.

b) The product from a) (1.2 g) was reacted with ammonia (50 ml, S.G.0.880) in 1,4-dioxane at 120° C. in a pressure vessel to give 7-cyclopentyl-5-[4-(2-methoxyphenoxy) phenyl]-7H-pyrrolo[2,3-d]pyrimidin-4-ylamine.

EXAMPLES 38a and 38b

2-[4-(4-Amino-7-cyclopentyl-7H-pyrrolo[2,3-d] pyrimidin-5-yl)phenoxy]phenol, m.p.107–109° C., (Example 38a) was prepared from 7-cyclopentyl-5-[4-(2-methoxy)phenoxyphenyl]-7H-pyrrolo[2,3-d]pyrimidin-4-ylamine (Example 38b) in a similar manner to Example 33.

EXAMPLE 39

N-[4-(4-Amino-7-cyclopentyl-7H-pyrrolo[2,3-d] pyrimidin-5-yl)-2-hydroxyphenyl]-4-chlorobenzamide is prepared in a similar manner to Example 33.

EXAMPLE 40

In a similar manner to Example 18, 7-cyclopentyl-5-(4-phenoxyphenyl)-7H-pyrrolo[2,3-d]pyrimidin-4-ylamine hemihydrate (2.5 g) was reacted with N-chlorosuccinimide (0.90 g) in dichloromethane (80 ml) to give 6-chloro-7-cyclopentyl-5-(4-phenoxyphenyl)-7H-pyrrolo[2,3-d]pyrimidin-4-ylamine.

EXAMPLE 41

A mixture of 4-amino-5-(4-phenoxyphenyl)-7-(tert-butyl)pyrrolo[2,3-d]-pyrimidine (5.8 g), glacial acetic acid (55 ml) and hydrobromic acid (55 ml of a 48% solution) was boiled under reflux for 18 hours under nitrogen. The mixture was allowed to cool and a solid was collected by filtration. This solid was washed with methanol and then with ether to give 4-amino-5-(4-phenoxyphenyl)-7H-pyrrolo[2,3-d]-pyrimidine hydrobromide, m.p. 288–292° C. The hydrobromide salt was converted into the free base by warming with dilute sodium hydroxide solution (100 ml of 5% w/v solution) and ethanol (60 ml) with stirring and removing the ethanol by distillation. The mixture was cooled and the solid was collected by filtration and washed well with water to give 5-(4-phenoxyphenyl)-7H-pyrrolo[2,3-d]pyrimidin-4-ylamine.

EXAMPLES 42–48 (General Method)

To a mixture of the fluorobenzene (1.25 molar equivalents) and potassium carbonate (2 molar equivalents) in a septum sealed tube was added, via a Gilson 215 liquid auto sampler, 4-amino-5-(4-hydroxyphenyl)-7-isopropylpyrrolo[2,3-d]pyrimidine (1 molar equivalent) as a stock solution in N,N-dimethylformamide (6 g in 240 ml). The reactions were heated, with shaking, at 120° C. for 4 hours and 140° C. for a further 1 hour and then evaporated to dryness in a centrifugal evaporator.

The reaction residues were dissolved in ethyl acetate/triethylamine (1 ml) (9:1) and eluted through a silica pad (3 g SiO$_2$: 12 mm diameter×20 mm height) with 9:1 ethyl acetate/triethylamine (4×2 ml). The combined column eluents were evaporated to yield the products as waxy solids, smears or expanded foams.

Reagent Quantities

| Example No. | Fluorobenzene (mg) | K$_2$CO$_3$ (mg) | Volume Phenol Solution |
|---|---|---|---|
| 42 | N-(2-fluoro-5-nitrophenyl)acetamide (91.5 mg) | 102 mg | 3960 µl |
| 43 | 5-fluoro-2-nitrobenzoic acid (88.6 mg) | 106 mg | 4105 µl |
| 44 | 2-fluoro-5-nitrobenzoic acid (84 mg) | 100 mg | 3892 µl |
| 45 | 5-fluoro-2-nitroanisole (80 mg) | 103 mg | 3934 µl |
| 46 | methyl 4-fluoro-3-nitrobenzoate (60 mg) | 67 mg | 2593 µl |
| 47 | 4-chloro-2-fluoronitrobenzene (86 mg) | 103 mg | 3994 µl |
| 48 | 2,2-dimethyl-2'-fluoro-5'-nitropropionanilide (63.5 mg) | 59 mg | 2267 µl |

Yields/LCMS

| Example | MF | Mwt | M+ found | % HPLC | Yield (mg) |
|---|---|---|---|---|---|
| 42 | C$_{23}$H$_{22}$N$_6$O$_4$ | 446.17 | Yes | 78.9 | 150 mg |
| 43 | C$_{22}$H$_{19}$N$_5$O$_5$ | 433.139 | Yes | 78.2 | 96.8 mg |
| 44 | C$_{22}$H$_{19}$N$_5$O$_5$ | 433.139 | Yes | 62.6 | 64.5 mg |
| 45 | C$_{23}$H$_{21}$N$_5$O$_4$ | 419.444 | Yes | 74.9 | 140.3 mg |
| 46 | C$_{23}$H$_{21}$N$_5$O$_5$ | 447.454 | Yes | 74.2 | 94.2 mg |
| 47 | C$_{21}$H$_{18}$ClN$_5$O$_3$ | 423.843 | Yes | 80.9 | 175.3 mg |
| 48 | C$_{26}$H$_{28}$N$_6$O$_4$ | 488.550 | Yes | 86.4 | 16.4 mg |

The compounds prepared in Examples 42 to 48 were:

EXAMPLE 42

N-{2-[4-(amino-7-isopropyl-7H-pyrrolo[2,3-d]pyrimidin-5-yl)phenoxy]-5nitrophenyl}acetamide;

EXAMPLE 43

5-[4-(4-amino-7-isopropyl-7H-pyrrolo[2,3-d]pyrimidin-5-yl)phenoxy]-2-nitrobenzoic acid;

EXAMPLE 44

2-[4-(4-amino-7-isopropyl-7H-pyrrolo[2,3-d]pyrimidin-5-yl)phenoxy]-5-nitrobenzoic acid;

EXAMPLE 45

7-isopropyl-5-[4-(3-methoxy-4-nitrophenoxy)phenyl]-7H-pyrrolo[2,3-d]pyrimidin-4-ylamine;

EXAMPLE 46 methyl 4-[4-(4-amino-7-isopropyl-7H-pyrrolo[2,3-d]pyrimidin-5-yl)phenoxy]-3-nitrobenzoate;

EXAMPLE 47

5-[4-(5-chloro-2-nitrophenoxy)phenyl]-7-isopropyl-7H-pyrrolo[2,3-d]pyrimidin-4-ylamine;

EXAMPLE 48

N-{2-[4-(4-amino-7-isopropyl-7H-pyrrolo[2,3-d]pyrimidin-5-yl)phenoxy]-5-nitrophenyl}-2,2-dimethylpropionamide;

EXAMPLE A

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

| | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

We claim:

1. Compounds of formula I

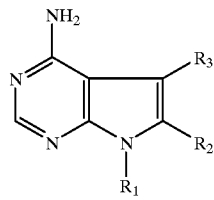

I including pharmaceutically acceptable salts thereof in which $R_1$ represents hydrogen, 2-phenyl-1,3-dioxan-5-yl, a $C_{1-6}$ alkyl group, a $C_{3-8}$ cycloalkyl group, a $C_{5-7}$ cycloalkenyl group or an (optionally substituted phenyl)$C_{1-6}$ alkyl group wherein the alkyl, cycloalkyl and cycloalkenyl groups are optionally substituted by one or more groups of formula $OR_A$ in which $R_A$ represents H or a $C_{1-6}$ alkyl group provided that a group of formula $OR_A$ is not located on the carbon attached to nitrogen;

$R_2$ represents hydrogen, a $C_{1-6}$ alkyl group, a $C_{3-8}$ cycloalkyl group, halo, hydroxy, an (optionally substituted phenyl)$C_{1-6}$ alkyl group, optionally substituted phenyl or $R_4$; and $R_3$ represents a group of formula (a)

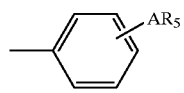

(a)

in which the phenyl ring is additionally optionally substituted and

A represents NH, O, NHSO$_2$, SO$_2$NH, a $C_{1-4}$ alkylene chain, NHCO, NHCO$_2$, CONH, NHCONH, CO$_2$ or S(O)$_p$ in which p is 0, 1 or 2, or A is absent and $R_5$ is attached directly to the phenyl ring;

and $R_5$ represents optionally substituted phenyl and, additionally, when A is absent $R_5$ represents a) a phthalimido group optionally substituted by halo or b) a pyrazolylamino group in which the pyrazole ring is optionally substituted by one or more of the following: hydroxy or optionally substituted phenyl;

$R_4$ represents a heterocyclic group selected from thienyl, benzo(b)thienyl, pyridyl, pyrazolyl, isoxazolyl, thiadiazolyl, oxadiazolyl, indazolyl, each of which is optionally substituted by one or more of the following: a $C_{1-6}$ alkyl group; a $C_{3-6}$ cycloalkyl group; a $C_{1-6}$ alkoxy group; a $C_{1-6}$ alkylthio group; hydroxy; optionally substituted phenyl; an (optionally substituted phenyl)$C_{1-6}$ alkyl group; an (optionally substituted phenyl)$C_{1-6}$ alkylthio group; or an (optionally substituted phenyl)$C_{1-6}$ alkoxy group;

wherein the term optionally substituted phenyl means phenyl optionally substituted by one or more of the following: a) a $C_{1-6}$ alkyl group, b) a $C_{1-6}$ alkoxy group, c) phenoxy, d) hydroxy, e) phenyl $C_{1-6}$ alkyl, f) halo, g) a group of formula $NR_{10}R_{11}$ in which $R_{10}$ and $R_{11}$ independently represent hydrogen, a $C_{1-6}$ alkyl group, phenyl, a $C_{1-6}$ alkanoyl group, a ($C_{1-6}$ alkoxy)carbonyl group, 5-hydroxy-1-phenyl-3-pyrazolyl or benzoyl which is optionally substituted by $C_{1-6}$ alkyl, $C_{1-6}$ alkoxy or halo h) a group of formula —COR$_9$ in which $R_9$ represents hydroxy, a $C_{1-6}$ alkoxy group, phenoxy or a group of formula $NR_{10}R_{11}$ in which $R_{10}$ and $R_{11}$ are as previously defined, i) a phthalimido group optionally substituted by halo, j) the phenyl ring is benz fused forming naphthyl or k) nitro.

2. Compounds according to claim 1 in which $R_1$ represents a $C_{1-6}$ alkyl group, a $C_{3-8}$ cycloalkyl group or an (optionally substituted phenyl)$C_{1-6}$ alkyl group wherein the alkyl and cycloalkyl groups are optionally substituted by one or more groups of formula $OR_A$ in which $R_A$ represents H or a $C_{1-6}$ alkyl group provided that a group of formula $OR_A$ is not located on the carbon attached to nitrogen;

$R_2$ represents hydrogen, a $C_{1-6}$ alkyl group, a $C_{3-8}$ cycloalkyl group, halo, hydroxy, an (optionally substituted phenyl)$C_{1-6}$ alkyl group, optionally substituted phenyl or $R_4$; and $R_3$ represents a group of formula (a)

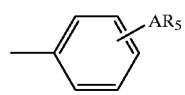

(a)

in which the phenyl ring is additionally optionally substituted and

A represents NH, O, NHSO$_2$, SO$_2$NH, a $C_{1-4}$ alkylene chain, NHCO, NHCO$_2$, CONH, NHCONH, CO$_2$ or S(O)$_p$ in which p is 0, 1 or 2, or A is absent and $R_5$ is attached directly to the phenyl ring;

and $R_5$ represents optionally substituted phenyl and, additionally, when A is absent $R_5$ represents a) a phthalimido group optionally substituted by halo or b) a pyrazolylamino group in which the pyrazole ring is optionally substituted by one or more of the following: hydroxy or optionally substituted phenyl;

$R_4$ represents a heterocyclic group selected from thienyl, benzo(b)thienyl, pyridyl, pyrazolyl, isoxazolyl, thiadiazolyl, oxadiazolyl, indazolyl, each of which is optionally substituted by one or more of the following: a $C_{1-6}$ alkyl group; a $C_{3-6}$ cycloalkyl group; a $C_{1-6}$ alkoxy group; a $C_{1-6}$ alkylthio group; hydroxy; optionally substituted phenyl; an (optionally substituted phenyl)$C_{1-6}$ alkyl group; an (optionally substituted phenyl)$C_{1-6}$ alkylthio group; or an (optionally substituted phenyl)$C_{1-6}$ alkoxy group;

wherein the term optionally substituted phenyl means phenyl optionally substituted by one or more of the following: a) a $C_{1-6}$ alkyl group, b) a $C_{1-6}$ alkoxy group, c) phenoxy, d) hydroxy, e) phenyl $C_{1-6}$ alkyl, f) halo, g)

a group of formula $NR_{10}R_{11}$ in which $R_{10}$ and $R_{11}$ independently represent hydrogen, a $C_{1-6}$ alkyl group, phenyl, a $C_{1-6}$ alkanoyl group, a $(C_{1-6}$ alkoxy)carbonyl group, 5-hydroxy-1-phenyl-3-pyrazolyl or benzoyl which is optionally substituted by $C_{1-6}$ alkyl, $C_{1-6}$ alkoxy or halo h) a group of formula —$COR_9$ in which $R_9$ represents hydroxy, a $C_{1-6}$ alkoxy group, phenoxy or a group of formula $NR_{10}R_{11}$ in which $R_{10}$ and $R_{11}$ are as previously defined, i) a phthalimido group optionally substituted by halo, or j) the phenyl ring is benz fused forming naphthyl.

3. Compounds according to claim 1 in which $R_1$ represents a $C_{3-6}$ alkyl group, a $C_{3-8}$ cycloalkyl group, or a $C_{5-7}$ cycloalkenyl group wherein the alkyl, cycloalkyl and cycloalkenyl groups are optionally substituted by one or more hydroxy groups provided that a hydroxy group is not located on the carbon attached to nitrogen.

4. Compounds according to claim 3 in which $R_1$ represents isopropyl, tert-butyl, 2-hydroxyethyl, cyclopentyl, neopentyl, 2-hydroxycyclopentyl, 4-hydroxycyclopent-2-enyl, 3-hydroxycyclopentyl, 2,3,4-trihydroxycyclopentyl, 1,3-dihydroxyprop-2-yl, or 2,3-dihydroxypropyl.

5. Compounds according to claim 1 in which $R_2$ represents hydrogen or halo.

6. Compounds according to claim 5 in which $R_2$ represents hydrogen or chloro.

7. Compounds according to claim 1 in which $R_3$ represents a group of formula (a)

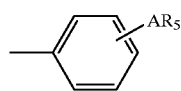

(a)

in which the phenyl ring is additionally optionally substituted and

A represents O, $NHSO_2$, NHCO, or $S(O)_p$ in which p is 0, 1 or 2, and $R_5$ represents optionally substituted phenyl.

8. Compounds according to claim 7 in which A represents $NHSO_2$.

9. Compounds according to claim 7 in which A represents NHCO.

10. Compounds according to claim 7 in which A represents O or S.

11. Compounds according to claim 7 in which A represents O.

12. Compounds according to claim 7 in which $R_3$ represents 2-phenoxyphenyl, 3-phenoxyphenyl, 4-phenoxyphenyl, 4-(phenylthio)-phenyl, 4-(4-methoxyphenoxy)phenyl, 4-(phenyl-sulphinyl)phenyl, 4-(phenyl-sulphonyl)phenyl,4-(4-hydroxyphenoxy) phenyl, 4-(benzenesulphonamido)phenyl, 4-(benzamido)phenyl, 4-(4-acetamidophenoxy)-phenyl), 4-(2-nitrophenoxy)phenyl,4-(4-aminophenoxy)phenyl, 4-(3-aminophenoxy)-phenyl, 4-(2-aminophenoxy)phenyl, 4-(3-acetamidophenoxy) phenyl, 4-[4-(N-methylacetamido)phenoxy]phenyl, 4-(2-acetamidophenoxy)phenyl, 4-(2-acetamido-4-nitrophenoxy)phenyl, 4-(3-carboxy-4-nitrophenoxy) phenyl, 4-(2-carboxy-4-nitrophenoxy)-phenyl, 4-(4-trifluoromethyl-2-nitrophenoxy)phenyl, 4-benzamido-3-methoxyphenyl, 4-benzamido-3-hydroxyphenyl, 4-benzenesulphonamido-3-methoxyphenyl, 4-benzenesulphonamido-3-hydroxy-phenyl, 3-hydroxy-4-(4-tert-butylbenzenesulphonamido) phenyl, 4-(2-hydroxyphenoxy)phenyl, 4-(4-chlorobenzamido)-3-hydroxyphenyl, 4-(3-methoxy-4-nitrophenoxy)phenyl, 4-(4-methoxycarbonyl-2-nitrophenoxy)-phenyl, 4-(4-carboxy-2-nitrophenoxy) phenyl, 4-(5-chloro-2-nitrophenoxy)phenyl, or 4-[4-nitro-2-(2,2-dimethylpropionamido)phenoxy]phenyl.

13. Compounds according to claim 1 in which $R_1$ represents methyl, ethyl, propyl, isopropyl, butyl, tert-butyl, benzyl, or 2-hydroxyethyl;

$R_2$ represents hydrogen, methyl, halo, hydroxy or phenyl and $R_3$ represents, 2-phenoxyphenyl, 3-phenoxyphenyl, 4-phenoxyphenyl, 4-(4-chloro-N-phthalimido)-3-tolyl, 3-chloro-4-(3-chlorophenoxy)phenyl, 4-(4-methylaminophenyl amino)phenyl, 4-(4-methylaminophenylamino)-2-methoxyphenyl, 4-(4-methylaminobenzyl)phenyl, 4-anilino-2-methoxyphenyl, 3-hydroxy-4-(4-methylbenzamido) phenyl, 3-hydroxy-4-(2-methoxybenzamido)phenyl, 4-(4-chlorobenzamido)-3-hydroxyphenyl, 3-hydroxy-4-(2-naphthalenesulphonamido)phenyl, 3-hydroxy-4-[4-(tert-butyl)-benzenesulphonamido]phenyl, 4-[N-(5-hydroxy-1-phenylpyrazol-3-yl)amino]phenyl, or 4-phenoxycarbonyl-amino-3-hydroxyphenyl.

14. Compounds according to claim 1 in which compounds of formula I are represented by formula Ib

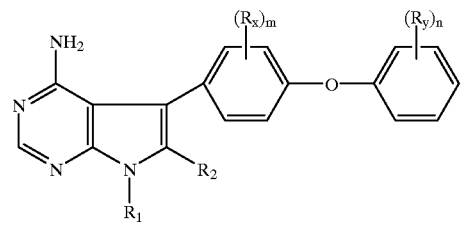

Ib and pharmaceutically acceptable salts thereof
in which
$R_1$ represents hydrogen, a $C_{1-6}$ alkyl group, a $C_{3-8}$ cycloalkyl group, a $C_{5-7}$ cycloalkenyl group or an (optionally substituted phenyl)$C_{1-6}$ alkyl group wherein the alkyl, cycloalkyl and cycloalkenyl groups are optionally substituted by one or more groups of formula $OR_A$ in which $R_A$ represents H or a $C_{1-6}$ alkyl group provided that a group of formula $OR_A$ is not located on the carbon attached to nitrogen;

$R_2$ represents hydrogen or halo;

$R_x$ represents a $C_{1-6}$ alkyl group, a $C_{1-4}$ alkoxy group, halo, or hydroxy;

$R_y$ represents a $C_{1-6}$ alkyl group, a $C_{1-4}$ alkoxy group, halo, hydroxy, nitro, or a group of formula $NR_{10}R_{11}$ in which $R_{10}$ and $R_{11}$ independently represent hydrogen, a $C_{1-6}$ alkyl group, phenyl, a $C_{1-6}$ alkanoyl group, a $(C_{1-6}$ alkoxy)carbonyl group or $R_y$ represents a group of formula –$COR_9$ in which $R_9$ represents hydroxy, a $C_{1-6}$ alkoxy group, phenoxy or a group of formula $NR_{10}R_{11}$ in which $R_{10}$ and $R_{11}$ are as previously defined;

and m and n independently represent 0, 1 or 2.

15. Compounds according to claim 14 in which $R_1$ represents a $C_{1-6}$ alkyl group, a $C_{3-8}$ cycloalkyl group, a $C_{5-7}$ cycloalkenyl group wherein the alkyl, cycloalkyl and cycloalkenyl groups are optionally substituted by one or more groups of formula $OR_A$ in which $R_A$ represents H or a $C_{1-6}$ alkyl group provided that a group of formula $OR_A$ is not located on the carbon attached to nitrogen.

16. Compounds according to claim 15 in which
$R_1$ represents isopropyl, tert-butyl, 2-hydroxyethyl, cyclopentyl, neopentyl, 2-hydroxycyclopentyl, 4-hydroxycyclopent-2-enyl, 3-hydroxycyclopentyl, 2,3,4-trihydroxycyclopentyl, 1,3-dihydroxyprop-2-yl, or 2,3-dihydroxypropyl.

17. Compounds according to claim 14 in which $R_2$ represents hydrogen or chloro.

18. Compounds according to claim 14 in which $R_x$ represents hydroxy or a $C_{1-4}$ alkoxy group.

19. Compounds according to claim 14 in which $R_y$ represents a $C_{1-4}$ alkyl group, a $C_{1-4}$ alkoxy group, nitro, acetamido, amino, N-methylacetamido, carboxy, hydroxy or halo.

20. Compounds according to claim 14 in which m represents 0 or 1.

21. Compounds according to claim 20 in which m represents 0.

22. Compounds according to claim 14 in which n represents 0 or 1.

23. Compounds according to claim 22 in which n represents 0 or 1 and $R_y$ represents hydroxy, amino or acetamido.

24. A compound selected from:
7-tert-butyl-5-(4-phenoxyphenyl)-7H-pyrrolo[2,3-d]pyrimidin-4-ylamine
7-tert-butyl-6-chloro-5-(4-phenoxyphenyl)-7H-pyrrolo[2,3-d]pyrimidin-4-ylamine
7-isopropyl-5-(4-phenoxyphenyl)-7H-pyrrolo[2,3-d]pyrimidin-4-ylamine
7-cyclopentyl-5-(4-phenoxyphenyl)-7H-pyrrolo[2,3-d]pyrimidin-4-ylamine
5-(4-biphenylyl)-7-tert-butyl-7H-pyrrolo[2,3-d]pyrimidin-4-ylamine
7-neopentyl-5-(4-phenoxyphenyl)-7H-pyrrolo[2,3-d]pyrimidin-4-ylamine 7-tert-butyl-5-[4-(phenylthio)phenyl]-7H-pyrrolo[2,3-d]pyrimidin-4-ylamine
7-tert-butyl-5-[4-(4-methoxyphenoxy)phenyl]-7H-pyrrolo[2,3-d]pyrimidin-4-ylamine
7-tert-butyl-5-[4-(phenylsulphinyl)phenyl]-7H-pyrrolo[2,3-d]pyrimidin-4-ylamine
7-tert-butyl-5-[4-(phenylsulphonyl)phenyl]-7H-pyrrolo[2,3-d]pyrimidin-4-ylamine
4-[4-(4-amino-7-tert-butyl-7H-pyrrolo[2,3-d]pyrimidin-5-yl)phenoxy]phenol
N-[4-(4-amino-7-isopropyl-7H-pyrrolo[2,3-d]pyrimidin-5-yl)phenyl]benzenesulphonamide
N-[4-(4-amino-7-isopropyl-7H-pyrrolo[2,3-d]pyrimidin-5-yl)phenyl]benzamide
N-{4-[4-(4-amino-7-tert-butyl-7H-pyrrolo[2,3-d]pyrimidin-5-yl)phenoxy]-phenyl}acetamide
7-isopropyl-5-[4-(2-nitrophenoxy)phenyl]-7H-pyrrolo[2,3-d]pyrimidin-4-ylamine
5-[4-(4-aminophenoxy)phenyl]-7-tert-butyl-7H-pyrrolo[2,3-d]pyrimidin-4-ylamine
5-[4-(3-aminophenoxy)phenyl]-7-tert-butyl-7H-pyrrolo[2,3-d]pyrimidin-4-ylamine
5-[4-(2-aminophenoxy)phenyl]-7-isopropyl-7H-pyrrolo[2,3-d]pyrimidin-4-ylamine
N-{3-[4-(4-amino-7-tert-butyl-7H-pyrrolo[2,3-d]pyrimidin-5-yl)phenoxy]phenyl}acetamide
N-{4-[4-(4-amino-7-tert-butyl-7H-pyrrolo[2,3-d]pyrimidin-5-yl)phenoxy]phenyl}-N-methylacetamide
N-{2-[4-(4-amino-7-isopropyl-7H-pyrrolo[2,3-d]pyrimidin-5-yl)phenoxy]phenyl}acetamide
N-{2-[4-(4-amino-7-isopropyl-7H-pyrrolo[2,3-d]pyrimidin-5-yl)phenoxy]-5-nitrophenyl}acetamide
5-[4-(4-amino-7-isopropyl-7H-pyrrolo[2,3-d]pyrimidin-5-yl)phenoxy]-2-nitrobenzoic acid
2-[4-(4-amino-7-isopropyl-7H-pyrrolo[2,3-d]pyrimidin-5-yl)phenoxy]-5-nitrobenzoic acid
2-[4-amino-5-(4-phenoxyphenyl)-7H-pyrrolo[2,3-d]pyrimidin-7-yl]ethanol
2-[4-amino-5-(4-phenoxyphenyl)-7H-pyrrolo[2,3-d]pyrimidin-7-yl]cyclopentanol
4-[4-amino-5-(4-phenoxyphenyl)-7H-pyrrolo[2,3-d]pyrimidin-7-yl]cyclopent-2-enol
6-chloro-7-cyclopentyl-5-(4-phenoxyphenyl)-7H-pyrrolo[2,3-d]pyrimidin-4-ylamine
5-(4-phenoxyphenyl)-7-(2-phenyl-1,3-dioxan-5-yl)-7H-pyrrolo[2,3-d]pyrimidin-4-ylamine
3-[4-amino-5-(4-phenoxyphenyl)-7H-pyrrolo[2,3-d]pyrimidin-7-yl]cyclopentanol
4-[4-amino-5-(4-phenoxyphenyl)-7H-pyrrolo[2,3-d]pyrimidin-7-yl]cyclopentan-1,2,3-triol
7-cyclopentyl-5-(2-phenoxyphenyl)-7H-pyrrolo[2,3-d]pyrimidin-4-ylamine
7-cyclopentyl-5-(3-phenoxyphenyl)-7H-pyrrolo[2,3-d]pyrimidin-4-ylamine
2-[4-amino-5-(4-phenoxyphenyl)-7H-pyrrolo[2,3-d]pyrimidin-7-yl]propan-1,3-diol
3-[4-amino-5-(4-phenoxyphenyl)-7H-pyrrolo[2,3-d]pyrimidin-7-yl]propan-1,2-diol
N-[4-(4-amino-7-cyclopentyl-7H-pyrrolo[2,3-d]pyrimidin-5-yl)-2-methoxyphenyl]benzamide
N-[4-(4-amino-7-cyclopentyl-7H-pyrrolo[2,3-d]pyrimidin-5-yl)-2-hydroxyphenyl]benzamide
N-[4-(4-amino-7-cyclopentyl-7H-pyrrolo[2,3-d]pyrimidin-5-yl)-2-methoxyphenyl]benzenesulphonamide
N-[4-(4-amino-7-cyclopentyl-7H-pyrrolo[2,3-d]pyrimidin-5-yl)-2-hydroxyphenyl]benzenesulphonamide
N-[4-(4-amino-7-cyclopentyl-7H-pyrrolo[2,3-d]pyrimidin-5-yl)-2-hydroxyphenyl]-4-tert-butylbenzenesulphonamide
7-cyclopentyl-5-[4-(2-methoxy)phenoxyphenyl]pyrrolo[2,3-d]pyrimidin-4-ylamine
2-[4-(4-amino-7-cyclopentyl-7H-pyrrolo[2,3-d]pyrimidin-5-yl)phenoxy]phenol
7-isopropyl-5-[4-(3-methoxy-4-nitrophenoxy)phenyl]-7H-pyrrolo[2,3-d]pyrimidin-4-ylamine
methyl 4-[4-(4-amino-7-isopropyl-7H-pyrrolo[2,3-d]pyrimidin-5-yl)phenoxy]-3-nitrobenzoate
4-[4-(4-amino-7H-pyrrolo[2,3-d]-pyrimidin-5-yl)phenoxy]phenol
N-[4-(4-amino-7-cyclopentyl-7H-pyrrolo[2,3-d]pyrimidin-5-yl)-2-methoxphenyl]-4-tert-butylbenzensulphonamide
7-cyclophentyl-5-[4-(2-methoxy)phenoxyphenyl]-7H-pyrrolo[2,3-d]pyrimidin-4-ylamine
N-[4-(4-amino-7-cyclopentyl-7H-pyrrolo[2,3-d]pyrimidin-5-yl)-2-hydroxy-phenyl]-4-chlorobenzamide
5-(4-phenoxyphenyl)-7H-pyrrolo[2,3-d]pyrimidin-4-ylamine
5-[4-(5-chloro-2-nitrophenoxy)phenyl]-7-isopropyl-7H-pyrrolo[2,3-d]pyrimidin-4-ylamine
N-{2-[4-(4-amino-7H-pyrrolo[2,3-d]pyrimidin-5-yl)phenoxy]-5-nitrophenyl}-2,2-dimethylpropionamide
and pharmaceutically acceptable salts thereof.

25. Pharmaceutical compositions containing a therapeutically effective amount of a compound of formula I or a salt thereof as described in claim 1 together with a pharmaceutically acceptable diluent or carrier.

26. A method of treating a proliferative disease and/or a disorder of the immune system which comprises the administration of a therapeutically effective amount of a compound of formula I as described in claim 1 to a mammal in need thereof, wherein said compound inhibits the activity of one or more protein tyrosine kinases thereby treating said proliferative disease and/or said disorder of the immune system.

27. A method of inhibiting a protein tyrosine kinase comprising contacting said protein tyrosine kinase with a compound of formula I of claim 1, wherein said contacting results in inhibition of the activity of said protein tyrosine kinase.

28. A process to prepare a compound of formula I according to claim 1 comprising a) condensing a compound of formula II

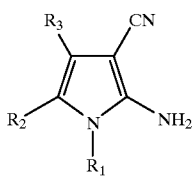

II in which $R_1$, $R_2$ and $R_3$ are as previously defined with formamide at a temperature in the range of 50 to 250° C. optionally in the presence of a catalyst; or b) reacting a compound of formula V

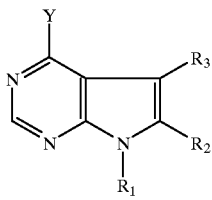

V in which $R_1$, $R_2$ and $R_3$ are as previously defined and Y represents a leaving group with ammonia or an ammonium salt at a temperature in the range of 15–250° C.; or c) reacting a compound of formula VIII

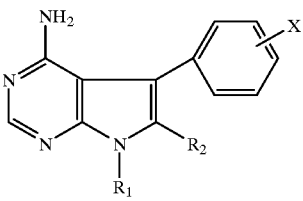

VIII in which $R_1$ and $R_2$ are as previously defined and X is halo with a compound of formula $R_5OH$ to give compounds of formula I in which $R_3$ represents $AR_5$ in which A represents O; or d) reacting a compound of formula IX

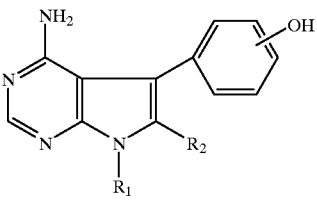

IX in which $R_1$ and $R_2$ are as previously defined with a compound of formula $R_5X$ in which X represents halo and $R_5$ is as previously defined to give compounds of formula I in which $R_3$ represents $AR_5$ in which A represents O and $R_5$ is as previously defined.

* * * * *